United States Patent
Kondo et al.

(10) Patent No.: US 9,663,447 B2
(45) Date of Patent: May 30, 2017

(54) ASYMMETRIC BUTADIENE-BASED CHARGE TRANSPORT COMPOUND, ELECTROPHOTOGRAPHIC PHOTORECEPTOR CONTAINING SAME, AND IMAGE FORMING APPARATUS

(71) Applicant: SAMSUNG ELECTRONICS CO., LTD., Suwon-si, Gyeonggi-do (KR)

(72) Inventors: Akihiro Kondo, Suwon-si (KR); Satoshi Katayama, Suwon-si (KR); Young-min Nam, Seongnam-si (KR); Won-joon Son, Seoul (KR); Chan-hee Lee, Seongnam-si (KR); Sang-heum Hwang, Seoul (KR)

(73) Assignee: S-PRINTING SOLUTION CO., LTD., Suwon-si (KR)

( * ) Notice: Subject to any disclaimer, the term of this patent is extended or adjusted under 35 U.S.C. 154(b) by 0 days.

(21) Appl. No.: 15/193,462

(22) Filed: Jun. 27, 2016

(65) Prior Publication Data

US 2016/0304437 A1 Oct. 20, 2016

Related U.S. Application Data

(63) Continuation of application No. PCT/KR2014/012889, filed on Dec. 26, 2014.

(30) Foreign Application Priority Data

Dec. 27, 2013 (KR) .................. 10-2013-0165641
Nov. 20, 2014 (KR) .................. 10-2014-0162604

(51) Int. Cl.
*G03G 5/047* (2006.01)
*C07C 211/58* (2006.01)
(Continued)

(52) U.S. Cl.
CPC .......... *C07C 211/58* (2013.01); *C07C 217/84* (2013.01); *G03G 5/0564* (2013.01); *G03G 5/0614* (2013.01); *G03G 5/0696* (2013.01)

(58) Field of Classification Search
CPC ... C07C 211/58; C07C 217/84; C07C 217/92; G03G 5/0614; G03G 5/0696; G03G 5/0564
See application file for complete search history.

(56) References Cited

U.S. PATENT DOCUMENTS 7,625,681 B2    12/2009    Kondoh et al.

FOREIGN PATENT DOCUMENTS

| JP | 1974-105536 | 10/1974 |
|----|-------------|---------|
| JP | 1979-058445 | 5/1979  |

(Continued)

OTHER PUBLICATIONS

Translation of JP 2004-175743 published Jun. 2004.*

(Continued)

*Primary Examiner* — Peter Vajda
(74) *Attorney, Agent, or Firm* — Staas & Halsey LLP

(57) ABSTRACT

Provided are an asymmetric butadiene-based charge transporting compound represented by one of Formula (1) and (1') as in claim 1, an electrophotographic photoreceptor including the asymmetric butadiene-based charge transporting compound, and an electrophotographic imaging apparatus. The electrophotographic photoreceptor including the organic photoconductive material as a charge transporting material may not cause a problem, such as partial crystallization during film formation and may have a high charge potential, a sufficient photoresponsive property with high sensitivity, and a high durability. Moreover, these properties may be all maintained even in the case of exposure to light (Continued)

as well as use in low-temperature environments or high-speed processes, thus having high reliability.

16 Claims, 2 Drawing Sheets

(51) Int. Cl.
*G03G 5/06* (2006.01)
*G03G 5/05* (2006.01)
*C07C 217/84* (2006.01)

(56) References Cited

FOREIGN PATENT DOCUMENTS

| | | |
|---|---|---|
| JP | 1979-059143 | 6/1979 |
| JP | 1979-150128 | 11/1979 |
| JP | 1979-151955 | 11/1979 |
| JP | 1980-052063 | 4/1980 |
| JP | 1983-198043 | 11/1983 |
| JP | 1990-051162 | 2/1990 |
| JP | 1990-190862 | 7/1990 |
| JP | 1994-043674 | 2/1994 |
| JP | 1995-048324 | 2/1995 |
| JP | 1998-069107 | 3/1998 |
| JP | 1998-239875 | 9/1998 |
| JP | 2004-175743 * | 6/2004 ............... G03G 5/06 |
| JP | 2006-323310 | 11/2006 |
| JP | 2011-186302 | 9/2011 |
| WO | WO 2015/099482 A1 | 7/2015 |

OTHER PUBLICATIONS

Written Opinion of the International Searching Authority (Form PCT/ISA/237); mailed Mar. 3, 2015 in corresponding International Patent Application No. PCT/KR2014/012889 (5 pages) (8 pages English Translation).

International Search Report (Form PCT/ISA/210); mailed Mar. 3, 2015 in corresponding International Patent Application No. PCT/KR2014/012889 (3 pages) (2 pages English Translation).

Form PCT/IB/306; Notification of the Recording of a Change; mailed Oct. 7, 2015 in corresponding International Application No. PCT/KR2014/012889 (1 page).

Form PCT/ISA/210; International Search Report; mailed Mar. 3, 2015 in corresponding International Application No. PCT/KR2014/012889 (3 pages) (2 pages English Translation).

Form PCT/IB/304; Notification Concerning Submission of a Priority Document; mailed Jan. 15, 2015 in corresponding International Application No. PCT/KR2014/012889 (1 page).

* cited by examiner

ASYMMETRIC BUTADIENE-BASED CHARGE TRANSPORT COMPOUND, ELECTROPHOTOGRAPHIC PHOTORECEPTOR CONTAINING SAME, AND IMAGE FORMING APPARATUS

CROSS-REFERENCE TO RELATED APPLICATIONS

This application is a continuation application of PCT international application PCT/KR2014/012889, filed on Dec. 26, 2014 and claims the benefits of Korean Patent Application No. 10-2013-0165641, filed on Dec. 27, 2013, and Korean Patent Application No. 10-2014-0162604, filed on Nov. 20, 2014, respectively, the contents are incorporated herein by reference.

TECHNICAL FIELD

The present disclosure relates to an organic photoconductive material, an electrophotographic photoreceptor including the organic photoconductive material, and an imaging apparatus.

BACKGROUND ART

Recently, organic photoconductive materials have been used in various devices, such as electrophotographic photoreceptors (hereinafter, also simply referred to as "photoreceptors"), electrostatic recording devices, sensor materials, or organic light-emitting devices (OLEDs).

An electrophotographic photoreceptor including an organic photoconductive material may be applied not only to photocopiers but also to other various devices, such as printing plates, slide films, micro films, and high-speed printers using laser, light-emitting diodes (LEDs) or cathode ray tubes (CRT) as a light source.

An organic photoreceptor including an organic photoconductive material may improve a film-forming property of a photosensitive layer, may have good flexibility, light weight, and good transparency. Accordingly, the organic photoreceptor may be readily used for designing a photoreceptor having good sensitivity over a wide range of wavelengths through an appropriate sensitization method. Accordingly, there has been an increasing need for an organic photoconductive material instead of an inorganic photoconductive material having a poor film-forming property, poor flexibility, high manufacturing cost, high toxicity, and limitations in manufacturing and handling, and an electrophotographic photoreceptor including the organic photoconductive material.

At the early stage of development, an organic photoreceptor has low sensitivity and durability. However, these drawbacks of the organic photoreceptor have been remarkably alleviated with the development of an electrophotographic photoreceptor including separate materials for specific functions, that is, a material with a charge generation function and a material with a charge transporting function.

The selection ranges for charge generating materials having a charge generation function and charge transporting materials having a charge transporting function for the electrophotographic photoreceptor including separate materials for specific functions are wide. Further, it is relatively easy to prepare an electrophotographic photoreceptor having any of such specific functions.

A variety of materials having strong resistance to light and good charge generation ability have been suggested as charge generating materials of the electrophotographic photoreceptor including separate materials for specific functions. Examples of the charge generating materials are phthalocyanine pigments, squarylium dyes, azo pigments, perylene pigments, polycyclic quinone pigments, cyanine dyes, squaric acid dyes, and pyrylium salt-based dyes.

Various compounds are known as charge transporting materials, such as, pyrazoline compounds as disclosed, for example, in Patent Document 1, hydrazone compounds as disclosed, for example, in Patent Documents 2, 3, and 4, triphenyl amine compounds as disclosed, for example, in Patent Documents 5 and 6, and stilbene compounds as disclosed, for example, in Patent Documents 7 and 8. More recently, pyrene derivatives, naphthalene derivatives, and terphenyl derivatives (such as terphenyl derivatives disclosed in Patent Document 9) that include a condensed polycyclic hydrocarbon system in a center mother nucleus thereof have been developed.

The characteristics required for the charge transporting materials are as follows:

(1) stability against light and heat, (2) stability against ozone, nitrogen oxide (NOx), and nitric acid, which are generated during the charging of a surface of the photoreceptor by corona discharge, (3) high charge transport ability, (4) high compatibility with an organic solvent or binder resin, (5) easy preparation and low costs, and the like.

However, the foregoing charge transporting materials meet only some of these requirements.

Further, the high charge transport ability of the foregoing characteristics requirements is more required than the other abilities. For example, when a charge transporting layer, in which a charge transporting material and a binder resin are dispersed, forms a surface layer of a photoreceptor, the charge transporting material has to have high charge transport ability to ensure a sufficient photoresponsive property.

When a photoreceptor is used in a copying machine or a laser beam printer, a part of a surface layer of the photoreceptor is inevitably scraped by a contact member, such as a cleaning blade or a charging roller. In order to improve the durability of the copying machine or the laser beam printer, a photoreceptor with a surface layer having strong scratch-resistance against the contact members is required.

Accordingly, to improve the durability of the surface layer, the amount of a binder resin in the charge transporting layer, that is, the surface layer, needs to be increased. However, this may deteriorate the photosensitive property of the photoreceptor. This is attributed to a reduction in the charge transporting ability of the charge transporting layer, due to dilution of the charge transport material in the charge transporting layer with the increased amount of the binder resin, in particular, when the charge transporting ability of the charge transporting material itself is poor.

The poor photoresponsive property of the photoreceptor may increase a residual surface potential of the photoreceptor. Repeated uses of the photoreceptor having such a high residual surface potential may not allow sufficient erasure of surface charges from a target exposure portion by exposure to light, and may deteriorate the image quality even at an early use stage. Thus, a charge transporting material having high charge transport ability is required to secure a sufficient photoresponsive property.

With the trends for small and high-speed electrophotographic devices, such as digital copiers and printers, a photoreceptor is more required to have a high sensitive property in order to be compatible with such high-speed processes.

Accordingly, higher charge transport ability is required for the charge transporting material. In particular, in high-speed printing processes, since the time taken from exposure to light to a development process is short, a photoreceptor having a high photoresponsive property is more required. As described above, the photoresponsive property of the photoreceptor depends on the charge transport ability of the charge transporting material. In this regard, a charge transporting material having higher charge transport ability is required.

A variety of compounds having charge mobility which is higher than those of the foregoing charge transporting materials have been suggested as charge transporting materials, for example, as disclosed in Patent Documents 10 to 14.

However, the photoreceptor using an enamine compound as disclosed in Patent Document 10, 11, or 12 does not exhibit satisfactory performance. The compound as disclosed in Patent Document 13 has a symmetric structure due to use of a bisbutadiene-based partial structure, and thus, has poor compatibility with a binder resin and may cause a partial crystallization during formation of a layer.

In order to address these problems, a bulky substituent, such as an aryl group, may be replaced with a small substituent, such as a methyl group; however, the aryl group is advantageous over an alkyl group in terms of electrical characteristics (e.g., hole mobility). Thus, there is a need for further improvement in this regard.

Furthermore, stable sensitivity without a reduction in low temperature environments and high reliability with less change of characteristics in various environments are required for the photoreceptor. However, a charge transporting material satisfying these requirements is not yet available.

[Patent Document 1] Japanese Patent Publication No. S52-004188
[Patent Document 2] Japanese Patent Publication No. S54-150128
[Patent Document 3] Japanese Patent Publication No. S55-042380
[Patent Document 4] Japanese Patent Publication No. S55-052063
[Patent Document 5] Japanese Patent Publication No. S58-032372
[Patent Document 6] Japanese Patent Publication No. H02-190862
[Patent Document 7] Japanese Patent Publication No. S54-151955
[Patent Document 8] Japanese Patent Publication No. S58-198043
[Patent Document 9] Japanese Patent Publication No. H07-048324
[Patent Document 10] Japanese Patent Publication No. H02-051162
[Patent Document 11] Japanese Patent Publication No. H06-043674
[Patent Document 12] Japanese Patent Publication No. H10-069107
[Patent Document 13] Japanese Patent Publication No. H10-239875
[Patent Document 14] Japanese Patent Publication No. 2011-186302

DETAILED DESCRIPTION OF THE INVENTION

Technical Problem

Provided is an organic photoconductive material for realizing a highly reliable electrophotographic photoreceptor, in which the organic photoconductive material may not cause partial crystallization during film formation and may have a high charge potential, high sensitivity, a sufficient photoresponsive property, high durability, and moreover, these properties may be all maintained even in the case of exposure to light as well as use in low-temperature environments or high-speed processes, thus having high reliability.

Provided is an electrophotographic photoreceptor including the organic photoconductive material.

Provided is an electrophotographic imaging apparatus including the organic photoconductive material.

Technical Solution

The inventors of the present disclosure have obtained a highly reliable electrophotographic photoreceptor by using an asymmetric butadiene-based compound, which has excellent compatibility with a binder resin, in a charge transporting layer of a laminated photosensitive layer or in a single-layered photosensitive layer, wherein the electrophotographic photoreceptor has a high charge potential, a sufficient photoresponsive property with high sensitivity, and a high durability. Moreover, these properties of the electrophotographic photoreceptor may be all maintained even in the case of exposure to light as well as use in low-temperature environments or high-speed processes, thus the electrophotographic photoreceptor having high reliability.

According to an embodiment, there is provided an asymmetric butadiene-based charge transporting compound represented by one of Formulae (1) and (1'):

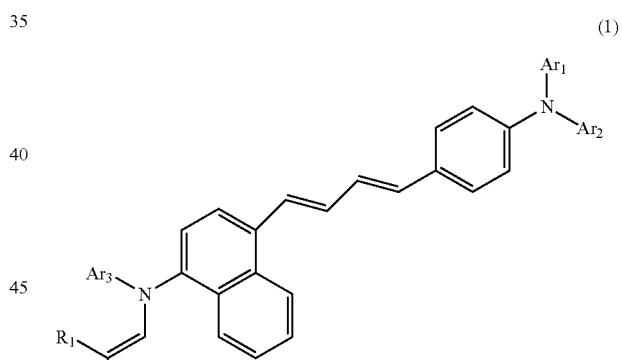

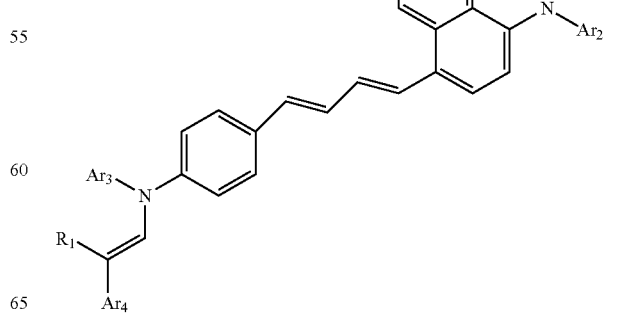

where, $Ar_1$, $Ar_2$, $Ar_3$, and $Ar_4$ are each independently a substituted or unsubstituted aryl group or a substituted or unsubstituted heteroaryl group, and R1 is independently a substituted or unsubstituted aryl group, a substituted or unsubstituted heteroaryl group, a substituted or unsubstituted aralkyl group, or a substituted or unsubstituted alkyl group.

According to another embodiment, there is provided an electrophotographic photoreceptor including a laminated photosensitive layer or a single-layered photosensitive layer on an electrically conductive substrate, the laminated photosensitive layer including a charge generating layer including a charge generating material and a charge transporting layer including a charge transporting material that are sequentially laminated in the stated order, the single-layered photosensitive layer including a charge generating material and a charge transporting material, wherein the charge transporting layer or the single-layered photosensitive layer includes at least one asymmetric butadiene-based compound as the charge transporting material, wherein the asymmetric butadiene-based compound is at least one compound selected from compounds represented by at least one of Formulae (1) and (1'):

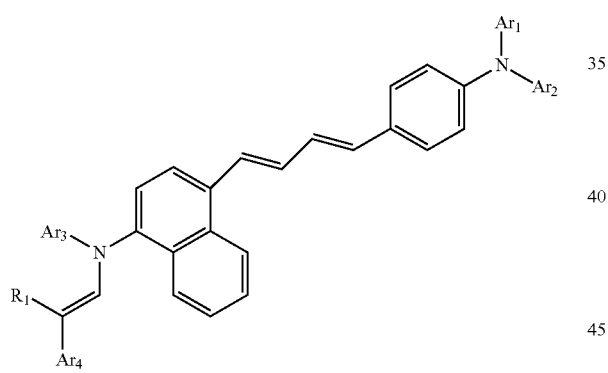

(1)

where, $Ar_1$, $Ar_2$, $Ar_3$, $Ar_4$, and R1 are the same as described above.

According to another embodiment, the asymmetric butadiene-based charge transporting compounds of Formulae (1) and (1') may be represented by one of Formulae (2) and (2'), respectively:

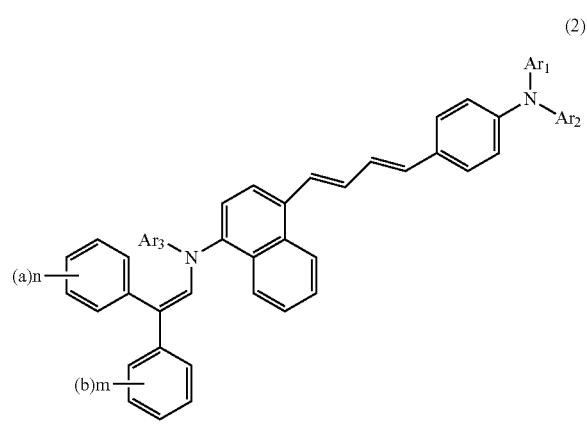

(2)

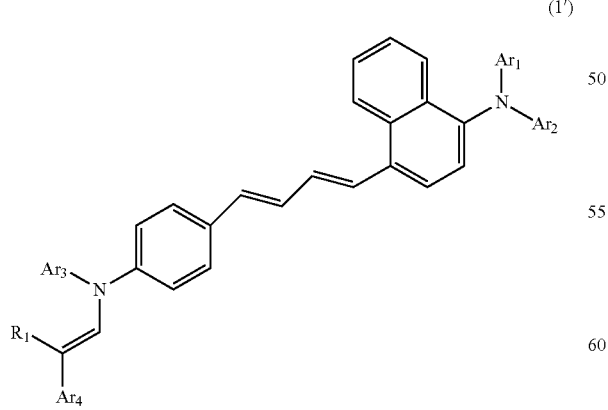

(2')

where a and b may be each independently a hydrogen atom, an alkyl group, an alkoxy group, or a dialkylamino group, m and n may be each independently an integer selected from 1 to 5, and $Ar_1$, $Ar_2$, and $Ar_3$ may be the same as described above.

According to another embodiment, the asymmetric butadiene-based charge transporting compounds of Formulae (1) and (1') may be represented by one of Formulae (3) and (3'), respectively:

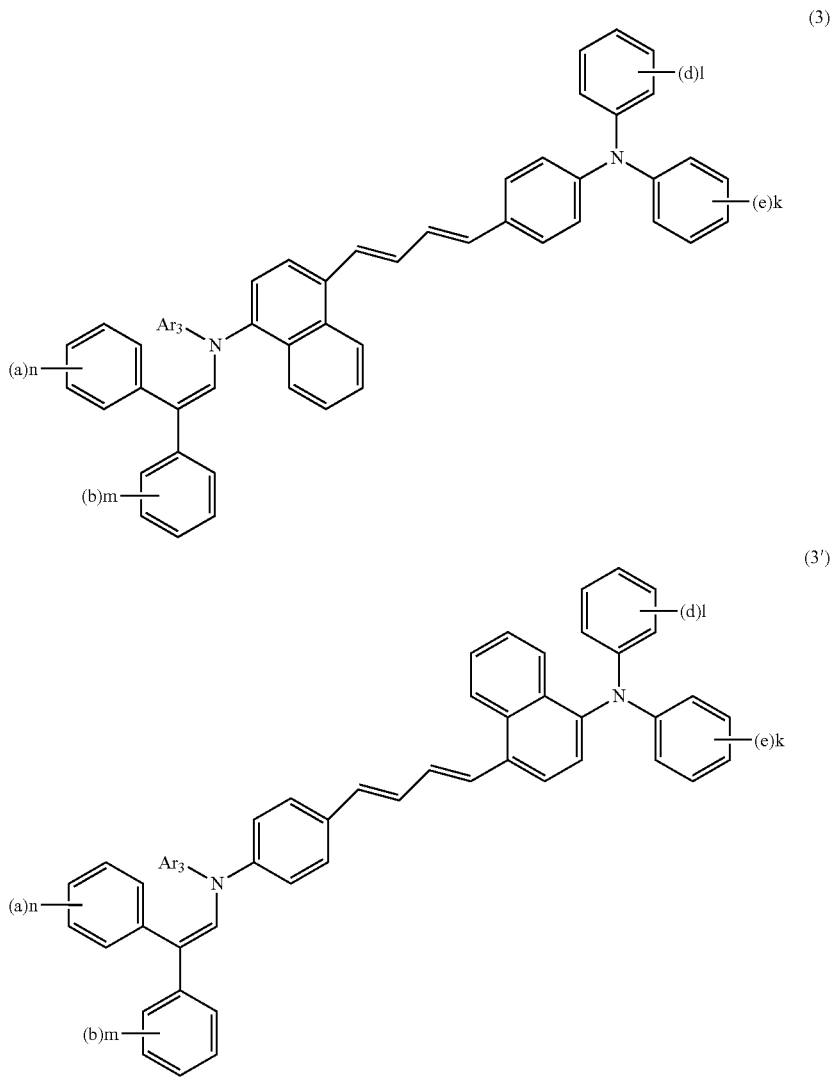

where a, b, d, and e may be each independently a hydrogen atom, an alkyl group, an alkoxy group, or a dialkylamino group, l, k, m, and n may be each independently an integer selected from 1 to 5, and $Ar_3$ may be the same as described above.

According to an embodiment of the electrophotographic photoreceptor, the charge transporting layer or the single-layered photosensitive layer may further include a binder resin, wherein a mass ratio (A:B) of the charge transporting material (A) to the binder resin (B) contained in the charge transporting layer or the single-layered photosensitive layer is in a range of about 10:12 to about 10:30.

According to another embodiment of the electrophotographic photoreceptor, the charge generating layer or the single-layered photosensitive layer may include oxotitanium phthalocyanine, which exhibits a diffraction peak at least at a Bragg angle)($2\theta \pm 0.2°$) of about 27.2° in a characteristic X-ray diffraction of Cu-Kα having a wavelength of about 1.54 Å, as the charge generating material.

According to another embodiment, the electrophotographic photoreceptor may further include an intermediate layer between either the laminated photosensitive layer or the single-layered photosensitive layer and the electrically conductive substrate.

According to another aspect of the present disclosure, there is provided an electrophotographic imaging apparatus including the electrophotographic photoreceptor according to an aspect of the present disclosure.

According to another embodiment, the electrophotographic imaging apparatus may form an image through a phase inversion development process.

Advantageous Effects of the Invention

According to the one or more embodiments of the present disclosure, the asymmetric butadiene-based compound represented by Formula (1) or (1'), which is used as an organic photoconductive material, may have high charge mobility. In the asymmetric butadiene-based compound of Formula (1) or (1'), different partial structures, for example, enamine structure and triarylamine structures, are bound to each of carbon atoms at the opposite terminals of a butadienyl group so as to disrupt molecular symmetry. Accordingly, the asymmetric butadiene-based compound of Formula (1) or (1') may have good compatibility with a binder resin and have high charge mobility without causing a drawback, such as partial crystallization during film formation.

According to the one or more embodiments of the present disclosure, when using the asymmetric butadiene-based compound of Formula (1) or (1') as a charge transporting material, a reliable electrophotographic photoreceptor may be obtained, which may have a high charge potential, a sufficient photoresponsive property with high sensitivity, and a high durability and may maintain the properties even in the case of exposure to light as well as use in low-temperature environments or high-speed processes.

The organic photoconductive material may be used in a sensor material, in an organic light-emitting device, or in an electrostatic recording device to provide an improved photoresponsive property.

According to the one or more embodiments of the present disclosure, a reliable electrophotographic photoreceptor may have a high charge potential, a sufficient photoresponsive property with high sensitivity, and a high durability, these properties being all maintained even in the case of use in low-temperature environments and high-speed processes, may be implemented by using the organic photoconductive material of Formula (1) or (1') having high charge mobility, for example, an organic photoconductive material of Formula (2), (2'), (3), or (3') above, as a charge transporting material in the photosensitive layer of the electrophotographic photoreceptor.

According to the one or more embodiments of the present disclosure, the photosensitive layer may include oxotitanium phthalocyanine, which exhibits a diffraction peak at least at a Bragg angle)(2θ±0.2° of about 27.2° in a characteristic X-ray diffraction of Cu-Kα having a wavelength of about 1.54 Å, as a charge generating material, and accordingly may have a high charge generation efficiency and a high charge injection efficiency. This charge generating material may generate a large amount of charges through light absorption and at the same time efficiently injects the generated charges into the charge transporting material 3, not accumulating the generated charges therein. In addition, as described above, the charge transporting material of Formula (1) or (1') that has high charge mobility is included in the photosensitive layer as an organic photoconductive material. Accordingly, charges generated from the charge generating material by light absorption may be efficiently injected into the charge transporting material to facilitate charge transfer. Thus, the electrophotographic photoreceptor with the photosensitive layer may have high sensitivity and high resolution.

According to the one or more embodiments of the present disclosure, a photosensitive layer may have a laminated structure in which a charge generating layer including a charge generating material and a charge transporting layer including a charge transporting material are stacked over one another. Due to the provision of the separate layers for charge generation and charge transport functions, optimum materials for each function may be selected. Accordingly, the electrophotographic photoreceptor may have improved sensitivity, in addition to improved durability such that its properties remain stable even after repeated use.

According to the one or more embodiments of the present disclosure, the photoresponsive property of an electrophotographic photoreceptor may be maintained when a ratio (A:B) of a charge transporting material (A) to a binder resin (B) is about 10:12 to about 10:30 in the charge transporting layer, even when the proportion of the binder resin is higher than in an electrophotographic photoreceptor using a conventional charge transporting material. Accordingly, the charge transporting layer may have improved wear-resistance without deterioration of the photoresponsive property, and consequently, the electrophotographic photoreceptor may have improved durability.

According to the one or more embodiments of the present disclosure, an intermediate layer may between an electrically conductive substrate and a photosensitive layer to prevent injection of charges into the photosensitive layer from the electrically conductive substrate and prevent deterioration of the charging characteristics of the photosensitive layer. Accordingly, the reduction of surface charges of the photosensitive layer, excluding the surface charges on an area to be erased through exposure, may be suppressed, and image defects, such as fogging may be prevented. A defect on the surface of the electrically conductive substrate may be covered, so that the surface of the electrically conductive substrate may become uniform, and the film formability of the photosensitive layer may improve. The intermediate layer may improve the adhesion between the photosensitive layer and the electrically conductive substrate, thereby suppressing separation of the photosensitive layer from the electrically conductive substrate.

According to the one or more embodiments of the present disclosure, an electrophotographic imaging apparatus may include an electrophotographic photoreceptor.

According to the one or more embodiments of the present disclosure, an electrophotographic photoreceptor may be obtained, which may have a high charge potential, a sufficient photoresponsive property with high sensitivity, and a high durability and maintain the properties even in a low-temperature environments or high-speed processes. Accordingly, when using the electrophotographic photoreceptor, a highly reliable imaging apparatus that may provide high quality images in various environments may be obtained. In addition, the characteristics of the electrophotographic photoreceptor may not deteriorate even in the case of exposure to light. Accordingly, the image quality of the electrophotographic imaging apparatus may be maintained even when, for example, the electrophotographic photoreceptor is exposed to light during a maintenance process, thereby improving the reliability of the imaging apparatus.

BEST MODE

Figure 1:
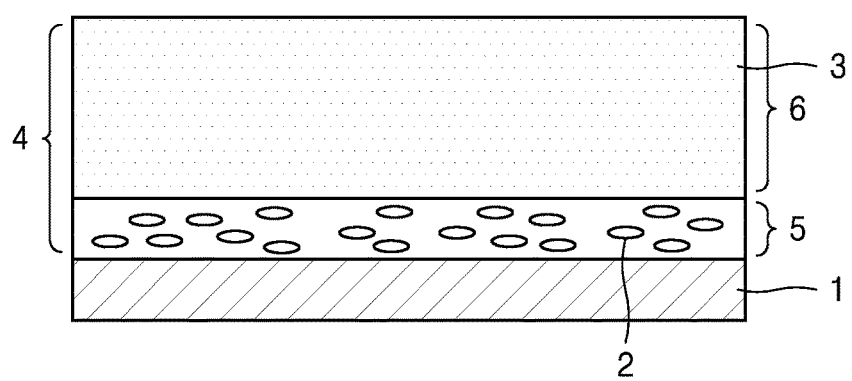
FIG. 1 is a schematic cross-sectional view illustrating an embodiment of an electrophotographic photoreceptor according to the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Hereinafter an organic photoconductive material, an electrophotographic photoreceptor including the organic photoconductive material, and an electrophotographic imaging apparatus according to various embodiments will be described in detail.

According to an embodiment of the present disclosure, an electrophotographic photoreceptor may include a photosensitive layer on an electrically conductive substrate. The photosensitive layer may be (1) a laminated photosensitive layer including a charge generating layer including a charge generating material and a charge transporting layer including a charge transporting material, the charge generating layer and the charge transporting layer being sequentially laminated in the stated order or (2) a single-layered photosensitive layer including a charge generating material and a charge transporting material. The charge transporting layer or the single-layered photosensitive layer may include an organic photoconductive material that comprises at least one asymmetric butadiene-based compound represented by one of Formulae (1) and (1'), as a charge transporting material:

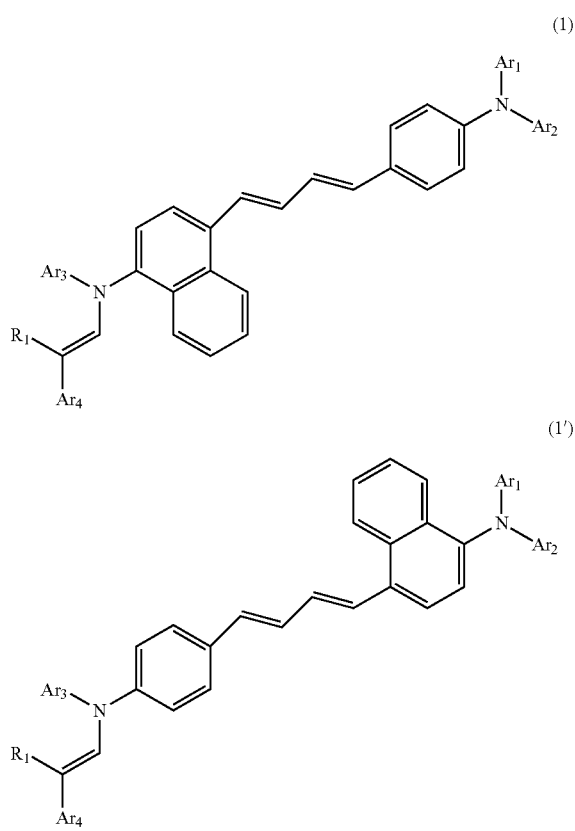

wherein, in any one of Formulae (1) and (1'), $Ar_1$, $Ar_2$, $Ar_3$, and $Ar_4$ may be each independently a substituted or unsubstituted aryl group or a substituted or unsubstituted heteroaryl group, and R1 may be independently a substituted or unsubstituted aryl group, a substituted or unsubstituted heteroaryl group, a substituted or unsubstituted aralkyl group, or a substituted or unsubstituted alkyl group. In some embodiments, $Ar_1$, $Ar_2$, $Ar_3$, and $Ar_4$ may be each independently a substituted or unsubstituted $C_6$ to $C_{18}$ aryl group, in some embodiments, a substituted or unsubstituted $C_6$ to $C_{12}$ aryl group, and in some embodiments, a substituted or unsubstituted $C_6$ to $C_9$ aryl group; or a substituted or unsubstituted $C_3$ to $C_{18}$ heteroaryl group, in some embodiments, a substituted or unsubstituted $C_3$ to $C_{12}$ heteroaryl group, and in some embodiments, a substituted or unsubstituted $C_4$ to $C_9$ heteroaryl group, and R1 may be a substituted or unsubstituted $C_6$ to $C_{18}$ aryl group, in some embodiments, a substituted or unsubstituted $C_6$ to $C_{12}$ aryl group, and in some embodiments, a substituted or unsubstituted $C_6$ to $C_9$ aryl group; a substituted or unsubstituted $C_3$ to $C_{18}$ heteroaryl group, in some embodiments, a substituted or unsubstituted $C_3$ to $C_{12}$ heteroaryl group, and in some embodiments, a substituted or unsubstituted $C_4$ to $C_9$ heteroaryl group; a substituted or unsubstituted $C_7$ to $C_{18}$ aralkyl group, in some embodiments, a substituted or unsubstituted $C_7$ to $C_{12}$ aralkyl group, and in some embodiments, a substituted or unsubstituted $C_7$ to $C_9$ aralkyl group; or a substituted or unsubstituted $C_1$ to $C_{10}$ alkyl group, in some embodiments, a substituted or unsubstituted $C_1$ to $C_6$ alkyl group, and in some embodiments, a substituted or unsubstituted $C_1$ to $C_4$ alkyl group.

Detailed examples of the substituted or unsubstituted $Ar_1$, $Ar_2$, $Ar_3$, and $Ar_4$ may include aryl groups, such as a phenyl group, a tolyl group, a methoxyphenyl group, a naphthyl group, a pyrenyl group, a biphenylyl group, a phenoxyphenyl group, a p-(phenylthio)phenyl group, and a p-styryl phenyl group; and heteroaryl groups, such as a furyl group, a thienyl group, a trimethylthienyl group, a thiazolyl group, a benzofuryl group, a benzothiophenyl group, a N-methyl indolyl group, a benzothiazolyl group, a benzoxazolyl group, and an N-ethyl carbazolyl group.

Detailed examples of the substituted or unsubstituted R1 may include aryl groups, such as a phenyl group, a tolyl group, a methoxyphenyl group, a naphthyl group, a pyreny group, a biphenylyl group, a phenoxyphenyl group, a p-(phenylthio) phenyl group, and a p-styryl phenyl group; heteroaryl groups, such as a furyl group, a thienyl group, a trimethylthienyl group, a thiazolyl group, a benzofuryl group, a benzothiophenyl group, an N-methyl indolyl group, a benzothiazolyl group, a benzoxazolyl group, and an N-ethyl carbazolyl group; aralkyl groups, such as a benzyl group, a p-methoxybenzyl group, and an 1-naphthylmethyl group; and alkyl groups, such as a methyl group, an ethyl group, a trifluoromethyl group, a fluoromethyl group, an isopropyl group, a t-butyl group, a cyclohexyl group, and a cyclopentyl group.

The organic photoconductive material comprising the asymmetric butadiene-based compound represented by one of Formulae (1) and (1') may have high charge mobility. By using the organic photoconductive material having a high charge mobility as a charge transporting material, a highly reliable electrophotographic photoreceptor may be obtained, which may have a high charge potential, a sufficient photoresponsive property with high sensitivity, and a high durability and may maintain the properties even in the case of exposure to light as well as use in low-temperature environments or high-speed processes. The organic photoconductive material may also be used in a sensor material, in an organic light-emitting device, or in an electrostatic recording device to provide an improved photoresponsive property.

In some embodiments, the asymmetric butadiene-based charge transporting compounds of Formulae (1) and (1') may be represented by one of Formulae (2) and (2'), respectively:

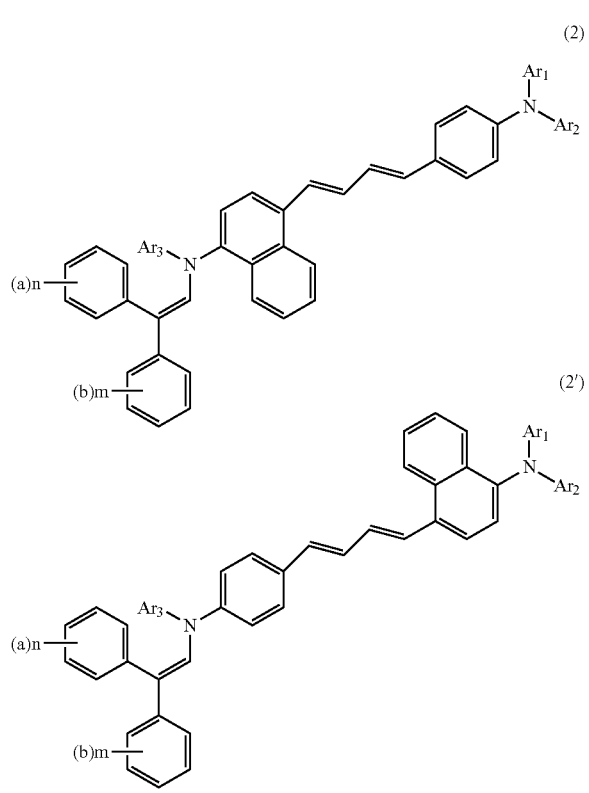

(2)

(2')

wherein, in any one of Formulae (2) and (2'), m and n indicate the numbers of the substituents a and b, respectively, and a and b indicate types of substituents. Here, m and n may be each independently an integer selected from 1 to 5. a and b may be each independently one selected from an alkyl group, an alkoxy group, an dialkylamino group, and a hydrogen atom. In Formulae (2) and (2'), when the number of a or b, that is, n or m, is 2 or greater, a's or b's may be identical to or different from each other. Detailed examples of a and b may include a hydrogen atom, an alkyl group, such as a methyl group, an ethyl group, an n-propyl group, an isopropyl group, a trifluoromethyl group, a fluoromethyl group, and an 1-methoxyethyl group; an alkoxy group, such as a methoxy group, an ethoxy group, a n-propoxy group, and an isopropoxy group; and a dialkylamino group, such as a dimethylamino group, a diethylamino group, and a diisopropylamino group.

The asymmetric butadiene-based compounds represented by Formulae (2) and (2') may have a particularly high charge mobility. The asymmetric butadiene-based compounds represented by Formulae (2) and (2') may be easily prepared. Accordingly, when the organic photoconductive materials of Formulae (1) and (1') are each specifically the asymmetric butadiene-based compound of one of Formulae (2) and (2'), it may be easy to obtain an organic photoconductive material having a particularly high charge mobility.

The organic photoconductive materials of Formulae (1) and (1') may each be an asymmetric butadiene-based compound represented by one of Formulae (3) and (3').

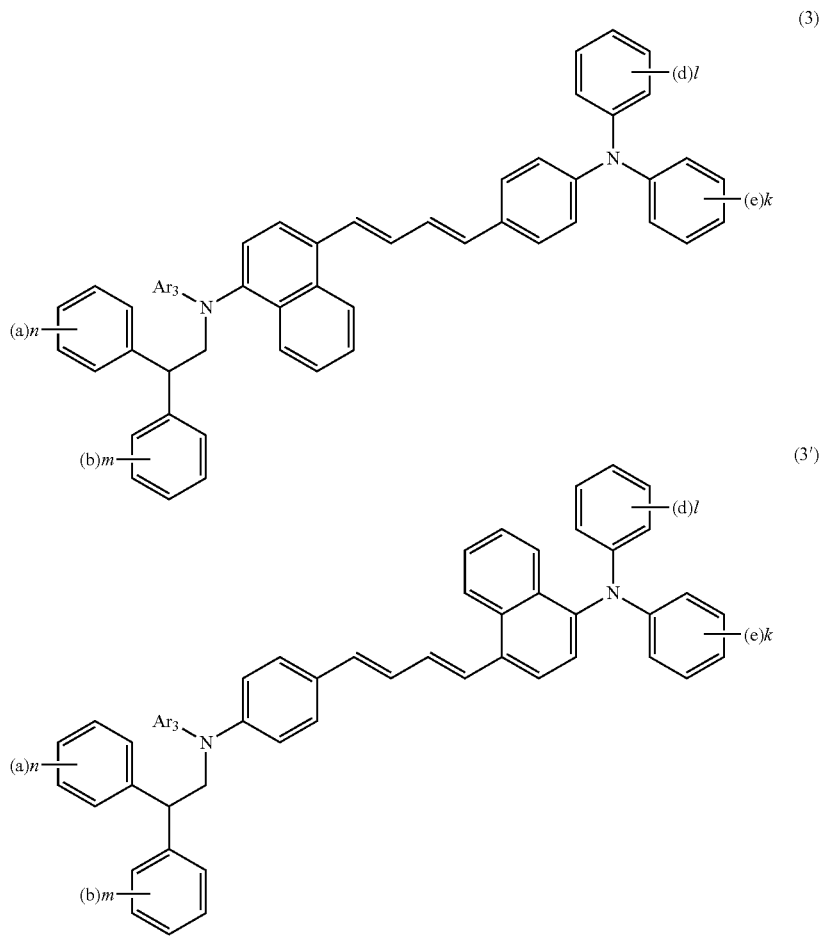

(3)

(3')

wherein, in any one of Formulae (3) and (3'), l, k, m, and n indicate the numbers of the substituents d, e, b, and a, respectively, and a, b, d, and e indicate types of substituents. l, k, m, and n may be each independently an integer selected from 1 to 5. a, b, d, and e may be each independently one selected from an alkyl group, an alkoxy group, a dialkylamino group, and a hydrogen atom. In Formulae (3) and (3'), when the number of a, b, d, or e is 2 or greater, a's, b's, d's or e's may be identical to or different from each other. Detailed examples of a, b, d, and e may include a hydrogen atom, an alkyl group, such as a methyl group, an ethyl group, an n-propyl group, an isopropyl group, a trifluoromethyl group, a fluoromethyl group, and an 1-methoxyethyl group; an alkoxy group, such as a methoxy group, an ethoxy group, a n-propoxy group, and an isopropoxy group; and a dialkylamino group, such as a dimethylamino group, a diethylamino group, and a diisopropylamino group.

The asymmetric butadiene-based compound represented by one of Formulae (3) and (3') may have a particularly high charge mobility. The asymmetric butadiene-based compounds represented by Formulae (3) and (3') may be easily prepared using a common raw material. Accordingly, when the organic photoconductive materials of Formulae (1) and (1') are each specifically the asymmetric butadiene-based compound of one of Formulae (3) and (3'), it may be easy to obtain an organic photoconductive material having a particularly high charge mobility.

Among the organic photoconductive material of one of Formulae (1) and (1'), a compound that is particularly excellent in terms of properties, cost, and productivity, may be, for example, one where $Ar_1$, $Ar_2$, $Ar_3$, $Ar_4$, and R1 are each a substituted or unsubstituted phenyl group.

Examples of the organic photoconductive material of Formulae (1) and (1') may include an exemplary compound having groups as represented in Table 1.

However, the organic photoconductive material of the present disclosure is not limited thereto. In Tables 1 and 2, $Ar_1$, $Ar_2$, $Ar_3$, $Ar_4$, and R1 correspond to those of one of Formulae (1) and (1'), respectively.

For example, when $Ar_1$ and $Ar_2$ in Formula (1) are p-tolyl groups, $Ar_3$ is a p-methoxyphenyl group, and $Ar_4$ and R1 are phenyl groups, the organic photoconductive material may be an exemplary compound 1 in Table 1, i.e., an asymmetric butadiene-based compound represented by Formula (4):

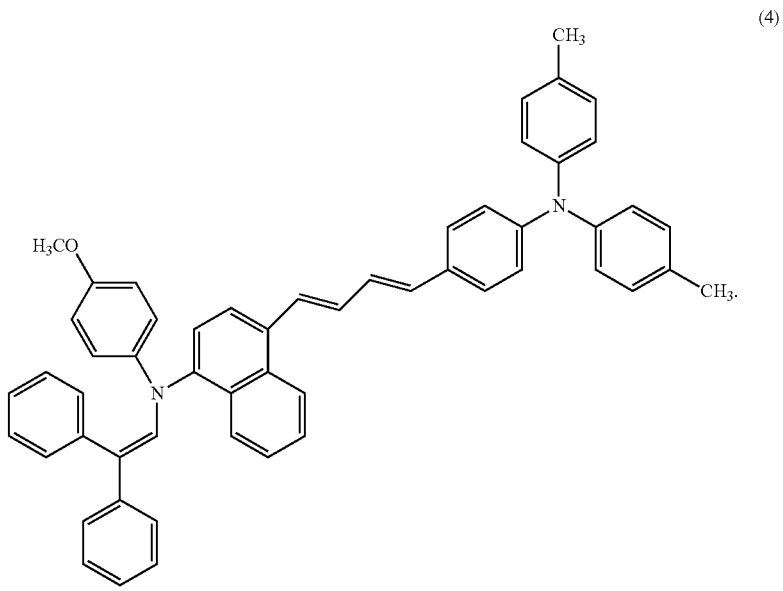 [SMILES: COc1ccc(N(C=C(c2ccccc2)c2ccccc2)c2ccc(/C=C/C=C/c3ccc(N(c4ccc(C)cc4)c4ccc(C)cc4)cc3)c3ccccc23)cc1]

When $Ar_1$ and $Ar_2$ in Formula (1') are p-tolyl groups, $Ar_3$ is a p-methoxyphenyl group, and $Ar_4$ and R1 are phenyl groups, the organic photoconductive material may be an exemplary compound 1' in Table 1, i.e., an asymmetric butadiene-based compound represented by Formula (4'):

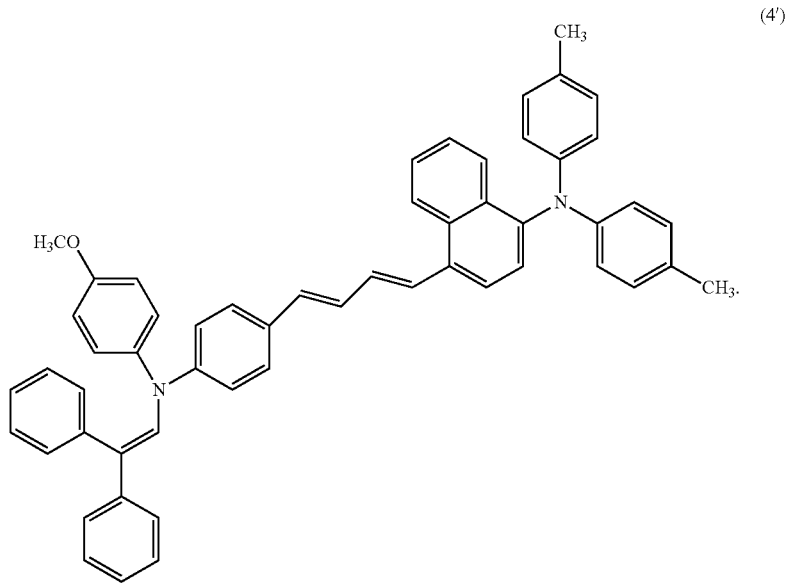 [SMILES: COc1ccc(N(C=C(c2ccccc2)c2ccccc2)c2ccc(/C=C/C=C/c3ccc(N(c4ccc(C)cc4)c4ccc(C)cc4)c4ccccc34)cc2)cc1]

(4')

As exemplified by compounds of Formulae (4) and (4'), in Tables 1 and 2, exemplary compounds first written, such as exemplary compounds 1, 2, and 3, fall within examples of the asymmetric butadiene-based compounds of Formula (1), and exemplary compounds second written, such as exemplary compounds 1', 2', and 3', fall within examples of the exemplary compound of the asymmetric butadiene-based compound of Formula (1').

TABLE 1

| Exemplary Compond No. | $Ar_1$ | $Ar_2$ | $Ar_3$ | $Ar_4$ | $R_3$ |
|---|---|---|---|---|---|
| 1/1' | —⌬—CH₃ (p-tolyl) | —⌬—CH₃ (p-tolyl) | —⌬—OMe | —⌬ (phenyl) | —⌬ (phenyl) |
| 2/2' | —⌬ (phenyl) | —⌬ (phenyl) | —⌬ (phenyl) | —⌬ (phenyl) | —⌬ (phenyl) |
| 3/3' | —⌬—OMe | —⌬—OMe | —⌬ (phenyl) | —⌬ (phenyl) | —⌬ (phenyl) |
| 4/4' | 3,4-dimethylphenyl | 3,4-dimethylphenyl | —⌬—CH₃ | —⌬ (phenyl) | —⌬ (phenyl) |
| 5/5' | 4-methyl-3-methoxyphenyl | 4-methyl-3-methoxyphenyl | —⌬ (phenyl) | —⌬ (phenyl) | —⌬ (phenyl) |

TABLE 1-continued

| Exemplary Compound No. | Ar₁ | Ar₂ | Ar₃ | Ar₄ | R₃ |
|---|---|---|---|---|---|
| 6/6' | 4-(tert-butyl)phenyl | 4-(tert-butyl)phenyl | phenyl | phenyl | phenyl |
| 7/7' | 4-(NMe₂)phenyl | 4-(NMe₂)phenyl | phenyl | phenyl | phenyl |
| 8/8' | 4-(OC₂H₅)phenyl | 4-(OC₂H₅)phenyl | phenyl | phenyl | phenyl |
| 9/9' | 2-methylphenyl | 2-methylphenyl | phenyl | phenyl | phenyl |
| 10/10' | 3-methyl-4-methoxyphenyl | 3-methyl-4-methoxyphenyl | phenyl | phenyl | phenyl |
| 11/11' | phenyl | phenyl | 4-methylphenyl | phenyl | phenyl |
| 12/12' | 4-methylphenyl | 4-methylphenyl | 4-methylphenyl | phenyl | phenyl |
| 13/13' | 4-methoxyphenyl | 4-methoxyphenyl | 4-methylphenyl | phenyl | phenyl |
| 14/14' | 3,4-dimethylphenyl | 3,4-dimethylphenyl | 4-methylphenyl | phenyl | phenyl |
| 15/15' | 3-methyl-4-methoxy-... (2-methyl-3-methoxyphenyl) | 2-methyl-3-methoxyphenyl | 4-methylphenyl | phenyl | phenyl |
| 16/16' | 4-(NMe₂)phenyl | 4-(NMe₂)phenyl | 4-methylphenyl | phenyl | phenyl |
| 17/17' | 4-(OC₂H₅)phenyl | 4-(OC₂H₅)phenyl | 4-methylphenyl | phenyl | phenyl |
| 18/18' | 2-methylphenyl | 2-methylphenyl | 4-methylphenyl | phenyl | phenyl |

TABLE 1-continued

| Exemplary Compound No. | Ar₁ | Ar₂ | Ar₃ | Ar₄ | R₃ |
|---|---|---|---|---|---|
| 19/19' | 4-OMe-3-CH₃-phenyl | 4-OMe-3-CH₃-phenyl | 4-CH₃-phenyl | phenyl | phenyl |
| 20/20' | phenyl | phenyl | 4-CH₃-phenyl | phenyl | phenyl |

TABLE 2

| Exemplary Compound No. | Ar₁ | Ar₂ | Ar₃ | Ar₄ | R₃ |
|---|---|---|---|---|---|
| 21/21' | 4-CH₃-phenyl | 4-CH₃-phenyl | phenyl | phenyl | phenyl |
| 22/22' | 4-OMe-phenyl | 4-OMe-phenyl | 4-OMe-phenyl | phenyl | phenyl |
| 23/23' | 4-CH₃-3-CH₃-phenyl | 4-CH₃-3-CH₃-phenyl | 4-OMe-phenyl | phenyl | phenyl |
| 24/24' | 4-CH₃-3-OMe-phenyl | 4-CH₃-3-OMe-phenyl | 4-OMe-phenyl | phenyl | phenyl |
| 25/25' | 2-CH₃-phenyl | 2-CH₃-phenyl | 4-OMe-phenyl | phenyl | phenyl |
| 26/26' | 4-OMe-3-CH₃-phenyl | 4-OMe-3-CH₃-phenyl | 4-OMe-phenyl | phenyl | phenyl |
| 27/27' | 4-CH₃-phenyl | 4-CH₃-phenyl | 4-CH₃-3-CH₃-phenyl | phenyl | phenyl |
| 28/28' | 4-OMe-phenyl | 4-OMe-phenyl | 4-OMe-3-CH₃-phenyl | phenyl | phenyl |

TABLE 2-continued

| Exemplary Compound No. | Ar₁ | Ar₂ | Ar₃ | Ar₄ | R₃ |
|---|---|---|---|---|---|
| 29/29' | 4-MeO-C₆H₄- | 4-MeO-C₆H₄- | 4-MeO-3-Me-C₆H₃- | C₆H₅- | C₆H₅- |
| 30/30' | 4-MeO-C₆H₄- | 4-MeO-C₆H₄- | 4-MeO-3-Me-C₆H₃- | C₆H₅- | C₆H₅- |
| 31/31' | 2-naphthyl | 4-Me-C₆H₄- | C₆H₅- | C₆H₅- | C₆H₅- |
| 32/32' | 1-naphthyl | 4-Me-C₆H₄- | C₆H₅- | C₆H₅- | C₆H₅- |
| 33/33' | 2-benzofuranyl | 2-benzofuranyl | C₆H₅- | C₆H₅- | C₆H₅- |
| 34/34' | 2-benzothienyl | 2-benzothienyl | C₆H₅- | C₆H₅- | C₆H₅- |
| 35/35' | 1-Me-2-indolyl | 1-Me-2-indolyl | C₆H₅- | C₆H₅- | C₆H₅- |
| 36/36' | 4-Me-C₆H₄- | 4-Me-C₆H₄- | 4-MeO-3-Me-C₆H₃- | 4-Me-C₆H₄- | 4-Me-C₆H₄- |
| 37/37' | 4-Me-C₆H₄- | 4-Me-C₆H₄- | C₆H₅- | 4-Me-C₆H₄- | 4-Me-C₆H₄- |
| 38/38' | 4-EtO-C₆H₄- | 4-EtO-C₆H₄- | C₆H₅- | 4-Me-C₆H₄- | 4-Me-C₆H₄- |
| 39/39' | 2-Me-C₆H₄- | 2-Me-C₆H₄- | C₆H₅- | 4-Me-C₆H₄- | 4-Me-C₆H₄- |
| 40/40' | 4-MeO-3-Me-C₆H₃- | 4-MeO-3-Me-C₆H₃- | C₆H₅- | 4-Me-C₆H₄- | 4-Me-C₆H₄- |

The organic photoconductive material of the asymmetric butadiene-based compound represented by one of Formulae (1) and (1') may have high charge mobility. When using the organic photoconductive material according to an embodiment having a high charge mobility as a charge transporting material, a reliable electrophotographic photoreceptor may be obtained, which may have a high charge potential, a sufficient photoresponsive property with high sensitivity, and a high durability and may maintain the properties even in the case of exposure to light as well as use in low-temperature environments or high-speed processes. The organic photoconductive material may also be used, for example, in a sensor material, in an organic light-emitting device, or in an electrostatic recording device to provide an improved photoresponsive property.

The asymmetric butadiene-based compound represented by Formula (1) as an organic photoconductive material may be prepared, for example, as follows.

First, a Wittig reagent represented by Formula (5):

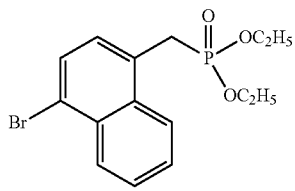

(5)

and a 4-iodocinnamoyl aldehyde derivative represented by Formula (6):

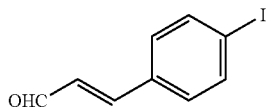

(6)

may be reacted via a Wittig reaction in an ether-based solvent, e.g., tetrahydrofuran (THF), diethyl ether, or ethylene glycol dimethyl ether, with a metal alkoxide, e.g., potassium-t-butoxide or sodium methoxide, to obtain a butadiene-based intermediate (A) represented by Formula (7):

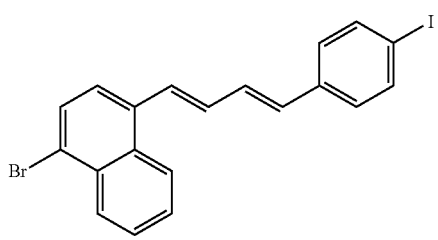

(7)

which is substituted at particular positions with different halogen elements.

Next, the butadiene-based intermediate (A) of Formula (7) and a secondary arylamine derivative represented by Formula (8):

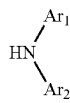

(8)

(wherein, in Formula (8), $Ar_1$ and $Ar_2$ may be each independently a substituted or unsubstituted aryl group or a substituted or unsubstituted heteroaryl group) may be mixed in a molar ratio of 1:0.95 and then subjected to an aryl amination reaction with palladium (Pd) as a catalyst. The aryl amination reaction may be performed under a slightly mild heating condition to allow selective substitution of the secondary arylamine derivative only with an iodine atom to synthesize an amine intermediate (B) represented by Formula (9):

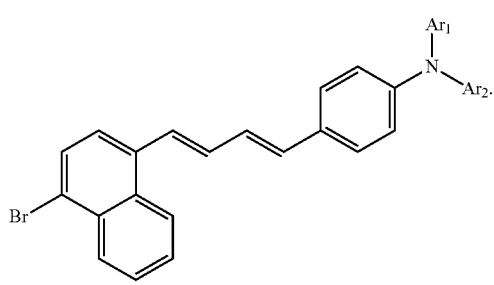

(9)

Next, the amine intermediate (B) of Formula (9) and a primary arylamine derivative represented by Formula (10):

(10)

(wherein, in Formula (10), $Ar_3$ may be a substituted or unsubstituted aryl group or a substituted or unsubstituted heteroaryl group) may be mixed in a molar ratio of 1:1.05 and then subjected to an aryl amination reaction with palladium (Pd) as a catalyst to synthesize a diamine intermediate (C) represented by Formula (11):

(11)

Lastly, the amine intermediate (C) of Formula (11) and an acetaldehyde derivative represented by Formula (12):

(12)

(wherein, in Formula (12), R1 may be a substituted or unsubstituted aryl group, a substituted or unsubstituted heteroaryl group, or a substituted or unsubstituted alkyl group, and $Ar_4$ may be a substituted or unsubstituted aryl group or a substituted or unsubstituted heteroaryl group) may be mixed in a solvent, e.g., toluene and xylene, which may be capable of forming an azeotrope with water in the presence of an acid catalyst, e.g., p-toluene sulfonic acid and camphorsulfonic acid, and then subjected to a dehydration reaction to prepare an asymmetric butadiene-based compound of Formula (1):

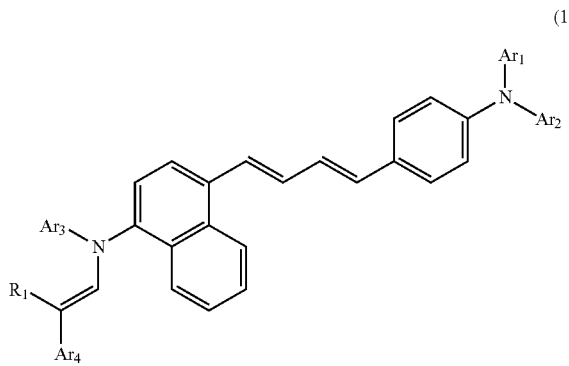

(1)

wherein, in Formula (1), $Ar_1$, $Ar_2$, $Ar_3$, $Ar_4$, and R1 may be the same as described above.

The asymmetric butadiene-based compound represented by Formula (1') as an organic photoconductive material may be prepared, for example, as follows.

First, a Wittig reagent represented by Formula (5'):

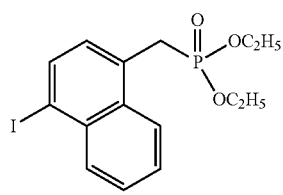

(5')

and a 4-bromocinnamoyl aldehyde derivative represented by Formula (6'):

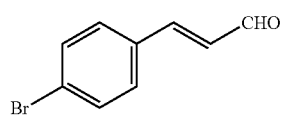

(6')

may be reacted via a Wittig reaction in an ether-based solvent, e.g., THF, diethyl ether, or ethylene glycol dimethyl ether, with a metal alkoxide, e.g., potassium-t-butoxide or sodium methoxide, to obtain a butadiene-based intermediate (A') represented by Formula (7'):

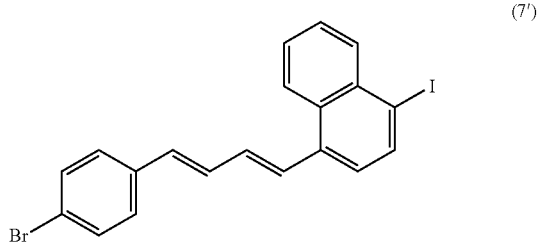 [SMILES: Brc1ccc(/C=C/C=C/c2ccc(I)c3ccccc23)cc1]

(7')

which is substituted at particular positions with different halogen atoms.

Next, the butadiene-based intermediate (A') of Formula (7') and a secondary arylamine derivative represented by Formula (8):

(8)

(wherein, in Formula (8), $Ar_1$ and $Ar_2$ may be each independently a substituted or unsubstituted aryl group or a substituted or unsubstituted heteroaryl group) may be mixed in a molar ratio of 1:0.95 and then subjected to an aryl amination reaction with palladium (Pd) as a catalyst. The aryl amination reaction may be performed under a slightly mild heating condition to allow selective substitution of the secondary arylamine derivative only with an iodine atom to synthesize an amine intermediate (B') represented by Formula (9'):

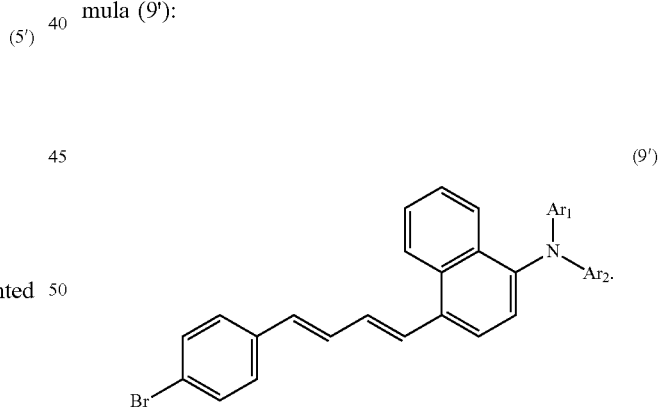

(9')

Next, the amine intermediate (B') of Formula (9') and a primary arylamine derivative represented by Formula (10):

$$H_2N—Ar_3 \quad (10)$$

(wherein, in Formula (10), $Ar_3$ may be a substituted or unsubstituted aryl group or a substituted or unsubstituted heteroaryl group) may be mixed in a molar ratio of 1:1.05 and then subjected to an aryl amination reaction with Pd as a catalyst to synthesize a diamine intermediate (C') represented by Formula (11'):

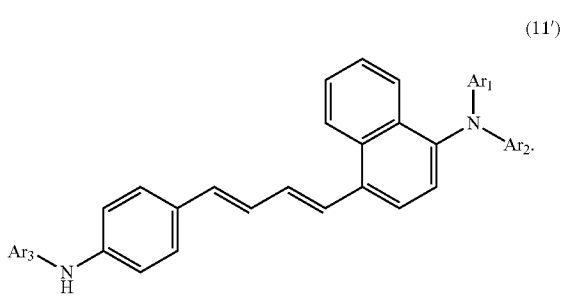

(11')

Lastly, the amine intermediate (C') of Formula (11') and an acetaldehyde derivative represented by Formula (12):

(12)

(wherein, in Formula (12), R1 may be a substituted or unsubstituted aryl group, a substituted or unsubstituted heteroaryl group, or a substituted or unsubstituted alkyl group, and $Ar_4$ may be a substituted or unsubstituted aryl group or a substituted or unsubstituted heteroaryl group) may be mixed in a solvent, e.g., toluene and xylene, which may be capable of forming an azeotrope with water in the presence of an acid catalyst, e.g., p-toluene sulfonic acid and camphorsulfonic acid, and then subjected to a dehydration reaction to prepare an asymmetric butadiene-based compound of Formula (1'):

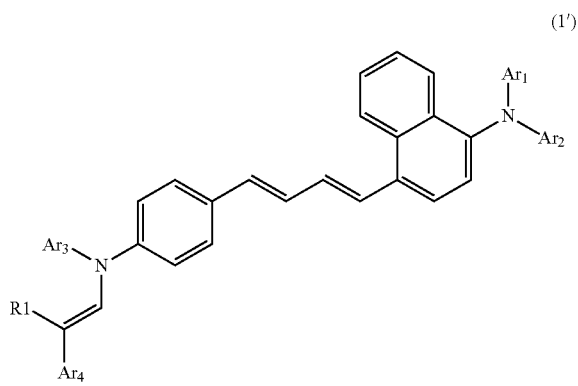

(1')

wherein, in Formula (1'), $Ar_1$, $Ar_2$, $Ar_3$, $Ar_4$, and R1 may be the same as described above.

According to embodiments of the present disclosure, the electrophotographic photoreceptor may be implemented in a variety of forms by using any of the organic photoconductive materials of one of Formulae (1) and (') described above as a charge transporting material. Hereinafter, the electrophotographic photoreceptor will be described with reference to the appended drawings.

Laminated Electrophotographic Photoreceptor

FIG. 1 is a schematic cross-sectional view illustrating a structure of an electrophotographic photoreceptor according to an embodiment of the present disclosure. Referring to FIG. 1, the electrophotographic photoreceptor may be a laminated electrophotographic photoreceptor including a photosensitive layer 4 having a laminated structure including a charge generating layer 5 including a charge generating material 2 and a charge transporting layer 6 including a charge transporting material 3 and a binder resin for binding the charge transporting material 3, which may be sequentially laminated on a sheet-type electrically conductive substrate 1 including a conductive material, in the stated order.

The charge generating material 2 and the charge transporting material 3 may be uniformly distributed in the components, such as the binder resin, of the charge generating layer 5 and the charge transport layer 6, respectively, although this is shown in an exaggerated fashion in FIG. 1.

The charge transporting material 3 in the charge transporting layer 6 may include at least one asymmetric butadiene-based compound of at least one of Formulae (1) and (1') having a high charge mobility, which is an organic photoconductive material according to an embodiment of the present disclosure. Accordingly, an electrophotographic photoreceptor may be obtained, which may have a high charge potential, a sufficient photoresponsive property with high sensitivity, and a high durability and maintain the properties even in low-temperature environments or high-speed processes.

As described above, the photosensitive layer 4 may have a laminated structure of the charge generating layer 5 including the charge generating material 2 and the charge transporting layer 6 including the charge transporting material 3. Due to the provision of the separate layers for charge generation and charge transport functions, optimum materials for each function may be selected. Accordingly, the electrophotographic photoreceptor may have improved sensitivity. The electrophotographic photoreceptor may also have improved durability such that its properties remain stable even after repeated use.

Electrically Conductive Substrate

The conductive material of an electrically conductive substrate 1 may be a metallic material, e.g., aluminum, an aluminum alloy, copper, zinc, stainless steel, and titanium, but is not limited thereto. Further, the conductive material of the electrically conductive substrate 1 may be a polymeric material, such as polyethylene terephthalate, nylon, and polystyrene; or hard paper or glass with a laminated metal foil on its surface, a deposited metal material, or a deposited or coated conductive compound, e.g., a conductive polymer, tin oxide, or indium oxide.

The electrically conductive substrate 1 of the electrophotographic photoreceptor of FIG. 1 may have a sheet form, but is not limited thereto. For example, the electrically conductive substrate 1 may have a hollow or solid cylindrical form or an endless belt form.

A surface of the electrically conductive substrate 1 may undergo a surface treatment using an anodic oxidation, chemicals, or a hydrothermal method; a coloring treatment; or a surface roughening treatment for inducing diffused reflection, unless the treatment affects adversely.

In an electrophotographic process using laser as an exposure light source, an incident laser beam may interfere with reflected light from the electrophotographic photoreceptor, thus generating an interference pattern that may cause an image defect. However, such an image defect caused by the interference of the laser light may be prevented through the foregoing treatments on the electrically conductive substrate 1.

Charge Generating Layer

The charge generating layer 5 may include the charge generating material 2 that may generate charges through light absorption, as a main component.

Charge Generating Material

Examples of the charge generating material may include azo-based pigments, such as monoazo-based pigments, bisazo-based pigments, and trisazo-based pigments; indigo-based pigments, such as indigo and thioindigo; perylene-based pigments, such as perylene imide and perylenic acid anhydride; polycyclic quinone-based pigments, such as anthraquinone and pyrenequinone; phthalocyanine-based pigments, such as metal phthalocyanine and metal-free phthalocyanine; squarylium dyes; pyrylium salts and thiopyrylium salts; triphenylmethane-based dyes; and inorganic materials such as selenium (Se) and amorphous silicon (Si). The foregoing charge generating materials may be used alone or in combination of at least two thereof.

Oxotitanium phthalocyanine from among these materials may be used as the charge generating material. Oxotitanium phthalocyanine is a charge generating material having both high charge generation and charge injection efficiencies, and thus generates a large amount of charges through light absorption and efficiently injects the generated charges into the charge transporting material 3, while not accumulating the generated charges within the charge generating material.

As described above, at least one organic photoconductive material of at least one of Formulae (1) and (1') having high charge mobility may be used as the charge transporting material 3.

Therefore, according to one or more embodiments, at least one charge transporting material of at least one of Formulae (1) and (1') may be used as a charge transporting material to efficiently transport the charges which are generated from the charge generating material 2 through light absorption and injected into the charge transporting material 3. Accordingly, an electrophotographic photoreceptor having high sensitivity and a high resolution may be obtained.

The charge generating material 2 may be used in combination with sensitizing dyes, such as triphenylmethane-based dyes, e.g., Methyl Violet, Crystal Violet, Night Blue, and Victoria Blue; acridine dyes, e.g., Erythrocin, Rhodamine B, Rhodamine 3R, Acridine Orange, and Flapeosine; thiazine dyes, e.g., Methylene Blue and Methylene Green; oxazine dyes, e.g., such as Capri Blue and Meldola's Blue; cyanine dyes; styryl dyes; and pyrylium salt dyes or thiopyrylium salt dyes.

Binder Resin for Charge Generating Layer

The binder resin may be, for example, one or a combination of at least two selected from the group consisting of a polyester, a polystyrene, a polyurethane, a phenolic resin, an alkyd resin, a melamine resin, an epoxy resin, a silicon resin, an acrylic resin, a methacrylic resin, a polycarbonate, a polyarylate, a phenoxy resin, a polyvinyl butyral, and a polyvinyl formal, and a copolymer resin including at least two different repeating units of the foregoing resins.

Examples of the copolymer resins may include insulating resins, e.g., a vinyl chloride-vinyl acetate copolymer, a vinyl chloride-vinyl acetate-maleic anhydride copolymer, and an acrylonitrile-styrene copolymer.

However, the binder resin is not limited thereto, and the binder resin may be a resin commonly used in the field.

Solvent for Charge Generating Layer Coating Solution

Examples of the solvent may include a halogenated hydrocarbon, e.g., dichloromethane and dichloroethane; ketones, e.g., acetone, methyl ethyl ketone, and cyclohexanone; esters, e.g., ethyl acetate and butyl acetate; ethers, e.g., THF and dioxane; ethylene glycol alkyl ethers, e.g., 1,2-dimethoxyethane; aromatic hydrocarbons, e.g., benzene, toluene, and xylene; or aprotic polar solvents, e.g., N,N-dimethyl formamide and N,N-dimethyl acetamide. The solvent may be a mixed solvent of at least two of the foregoing solvents.

Charge Generating Layer Coating Solution

A mixing ratio of the charge generating material 2 to the binder resin may be in a range such that the amount of the charge generating material 2 in the charge generating layer is in a range of about 10 mass % to about 99 mass %. When the amount of the charge generating material 2 is less than 10 mass %, the charge generating layer 5 may have low sensitivity. When the amount of the charge generating material 2 is greater than 99 mass %, the charge generating layer 5 may have weak strength and the charge generating material 2 may have poor dispersibility, thereby including more large coarse particles and reducing surface charges, other than the surface charges on an area to be erased through exposure. As a result, image defects, such as fogging of images due to fine black dots resulting from toner adhesion to white medium, are more likely to occur. Accordingly, the mixing ratio of the charge generating material 2 to the binder resin may be in the range such that the amount of the charge generating material 2 in the charge generating layer is in a range of about 10 mass % to about 99 mass %.

Charge Generating Layer Formation Method

The charge generating layer 5 may be formed by vacuum depositing the charge generating material 2 on the electrically conductive substrate 1 or by coating a charge generating layer coating solution obtained by dispersing the charge generating material 2 in a solvent, onto the electrically conductive substrate 1. Among these methods, the charge generating layer 5 may be formed by coating the charge generating layer coating solution onto the electrically conductive substrate 1, wherein the charge generating layer coating solution may be obtained by dispersing the charge generating material 2 by using a conventional known method into a binder resin solution obtained by mixing a binder resin and a solvent. Hereinafter this method will be described in detail.

Prior to the dispersing of the charge generating material 2 in the binder resin solution, the charge generating material 2 may be ground using a grinder. Examples of the grinder may include a ball mill, a sand mill, an attritor, a vibration mill, and an ultrasonic dispersing device.

Examples of a dispersing device used to disperse the charge generating material 2 in the binder resin solution may include a paint shaker, a ball mill, or a sand mill. The dispersion conditions may be appropriately selected to prevent incorporation of impurities generated from abrasion of a container used and members of the dispersing device.

Examples of the method of coating the charge generating layer coating solution obtained by dispersing the charge generating material 2 in the binder resin solution may include a spray method, a bar coating method, a roll coating method, a blade method, a ring method, and a dip coating method. An appropriate method may be selected from these coating methods by taking into account the physical properties of the charge generating layer coating solution and productivity.

The dip coating method may be used to form a layer on the electrically conductive substrate 1 by dipping the electrically conductive substrate 1 in a bath filled with a coating solution, and then drawing the conductive substrate 1 up from the bath at a constant speed or a varying speed. The dip coating method is relatively simple and is advantageous in terms of productivity and costs, and thus is mainly used in manufacturing an electrophotographic photoreceptor. An apparatus used in the dip coating method may be equipped with a coating solution dispersing device, such as an ultrasonic wave generator, to stabilize the dispersiblity of the coating solution.

The charge generating layer 5 may have a thickness in a range of about 0.05 µm to about 5 µm, and in some embodiments, in a range of about 0.1 µm to about 1 µm. When the thickness of the charge generating layer 5 is less than 0.05 µm, the light absorption efficiency of the charge generating layer 5 may decrease, thus reducing its sensitivity. When the thickness of the charge generating layer 5 is greater than 5 µm, charge migration inside the charge generating layer 5 may become a rate-determining stage of the process of erasing surface charges of the electrophotographic photoreceptor, thus lowering its sensitivity.

Charge Transporting Layer

The charge transporting layer 6 may be obtained by incorporating, as the charge transporting material 3, at least one organic photoconductive material of at least one of Formulae (1) and (1') into a binder resin, wherein the at least one organic photoconductive material may accept and transport the charges generated from the charge generating material 2.

Charge Transporting Material

At least one charge transporting material of at least one of Formulae (1) and (1') may be one or a combination of at least two selected from the group consisting of exemplary compounds 1 to 40 and exemplary compounds 1' to 40' in Tables 1 and 2. The at least one charge transporting material of at least one of Formulae (1) and (1') may be used in combination with other charge transporting materials.

Examples of the other charge transporting materials may include a carbazole derivative, an oxazole derivative, an oxadiazole derivative, a thiazole derivative, a thiadiazole derivative, a triazole derivative, an imidazole derivative, an imidazolone derivative, an imidazolidine derivative, a bisimidazolidine derivative, a styryl compound, a hydrazone compound, a polycyclic aromatic compound, an indole derivative, a pyrazoline derivative, an oxazolone derivative, a benzimidazole derivative, a quinazoline derivative, a benzofuran derivative, an acridine derivative, a phenazine derivative, an aminostilbene derivative, a triarylamine derivative, a triarylmethane derivative, a phenylenediamine derivative, a stilbene derivative, and a benzidine derivative. A polymer including a moiety derived from these compounds in a main chain or side chain, for example, such as poly-N-vinyl carbazole, poly-1-vinyl pyrene, and poly-9-vinyl anthracene, may also be used as the other charge transporting materials.

In order to realize high charge transporting ability, the at least one organic photoconductive material of at least one of Formulae (1) and (1') may be used alone as the charge transporting material 3.

Binder Resin for Charge Transporting Layer

As for a binder resin used in the charge transporting layer 6, a binder resin having good compatibility with the charge transporting material 3 may be selected. Examples of the binder resin may include a vinyl polymer, e.g., polymethyl methacrylate, polystyrene, polyvinylchloride, and copolymers thereof; and resins, e.g., a polycarbonate, a polyester, a polyester carbonate, a polysulfone, a phenoxy resin, an epoxy resin, a silicon resin, a polyarylate, a polyamide, a polyether, a polyurethane, a polyacrylamide, and a phenolic resin. For example, the binder resin may be a partially cross-linked thermosetting resin of these binder resins.

These binder resins may be used alone or in a combination of at least two. In some embodiments, the binder resin may be a polystyrene, a polycarbonate, a polyarylate, or a poly- phenylene oxide that has a volume resistance of about $10^{13}\Omega$ or greater, a good electrical insulating property, good film formability, and good potential characteristics.

As described above, due to the use of the charge transporting material 3 including the at least one organic photoconductive material of at least one of Formulae (1) and (1') that has a high charge mobility, the photoresponsive property may be maintained even with a ratio (A:B) of the charge transporting material (A) to the binder resin (B) ranging from about 10:12 to about 10:30, wherein the proportion of the binder resin (B) is higher than when using a conventional charge transporting material. Accordingly, the charge transporting layer 6 may allow the electrophotographic photoreceptor to have improved printing durability without deterioration of the photoresponsive property, and consequently, the electrophotographic photoreceptor may have improved durability.

When the ratio (A:B) is less than 10:30 with a higher proportion of the binder resin and the charge transporting layer 6 is formed by a dip coating method, the viscosity of a coating solution may increase, which reduces the coating speed and productivity.

When the amount of a solvent in the coating solution is increased to suppress the viscosity increase of the coating solution, a blushing phenomenon may occur, resulting in white turbidity of the charge transporting layer 6. When the ratio (A:B) is greater than 10:12 with a lower proportion of the binder resin, the printing durability of the charge transporting layer 6 may decrease, as compared with the case of using the higher proportion of the binder resin, and the abrasion of the photosensitive layer may increase.

Accordingly, according to embodiments of the present disclosure, the mass ratio (A:B) of the charge transporting material (A) to the binder resin (B) in an electrophotographic photoreceptor may be in the range of about 10:12 to about 10:30, unlike a conventional mass ratio of charge transporting material to binder resin of about 10:12.

Additives for Charge Transporting Layer

To improve film formability, flexibility, and surface smoothness of the charge transporting layer 6, an additive, such as a platicizer or a leveling agent, may be added to the charge transporting layer 6. Examples of the platicizer may include a dibasic acid ester, a fatty acid ester, a phosphoric acid ester, a phthalic acid ester, chlorinated paraffin, and an epoxy-type plasticizer. An example of the leveling agent may include a silicon-based leveling agent.

To improve the mechanical strength or electrical characteristics of the charge transporting layer 6, particles of an inorganic compound or an organic compound may be added to the charge transporting layer 6. Any suitable additives, such as, an antioxidant and a sensitizer, may be added to the charge transporting layer 6, if necessary. The addition of additives may improve potential characteristics of the photoreceptor and stability of the coating solution, and may reduce fatigue deterioration due to repeated use of the photoreceptor and also improve the durability of the photoreceptor.

An example of the antioxidant may include a hindered phenol derivative or a hindered amine derivative. The amount of the hindered phenol derivative may be in a range of about 0.1 mass % to about 50 mass % based on the amount of the charge transporting material 3. The amount of the hindered amine derivative may be in a range of about 0.1 mass % to about 50 mass % based on the amount of the charge transporting material 3. A mixture of a hindered phenol derivative and a hindered amine derivative may be used. In this case, the total amount of the hindered phenol derivative and the hindered amine derivative may be in a range of about 0.1 mass % to about 50 mass % based on the amount of the charge transporting material 3. When the amount of the hindered phenol derivative or the hindered amine derivative, or the total amount of the two is less than 0.1 mass %, improvements in the stability of the coating solution and the durability of the photoreceptor may not be satisfactory. When the amount of the hindered phenol derivative or the hindered amine derivative or the total amount of the two is greater than 50 mass %, the characteristics of the photoreceptor may be adversely affected.

Method of Forming Charge Transporting Layer

The charge transporting layer 6 may be formed by the same method used in forming the charge generating layer 5. For example, the charge transporting material 3 and a binder resin, and any of the foregoing additives if required, may be dissolved or dispersed in an appropriate solvent to prepare a charge transporting layer coating solution. The charge transporting layer coating solution may be coated on the charge generating layer 5 by using a spray method, a bar coating method, a roll coating method, a blade method, a ring method, or a dip coating method to form the charge transporting layer 6. Among these coating methods, the dip coating method is advantageous in various aspects as described above, and thus is mainly used to form the charge transporting layer 6.

An appropriate solvent for the charge transporting layer coating solution may be one or a mixture of at least two selected from the group consisting of an aromatic hydrocarbon, such as benzene, toluene, xylene, and monochlorobenzene; a halogenated hydrocarbon, such as dichloromethane and dichloroethane; an ether, such as THF, dioxane, and dimethoxymethyl ether; and an aprotic polar solvent, such as N,N-dimethylformamide. A further solvent, such as an alcohol, acetonitrile, or methyl ethyl ketone, may be added to the foregoing solvent, if necessary.

The thickness of the charge transporting layer 6 may be in a range of about 5 μm to about 50 μm, and in some embodiments, in a range of about 10 μm to about 40 μm. When the thickness of the charge transporting layer 6 is less than 5 μm, the photoreceptor may have poor surface charge retainability. When the thickness of the charge transporting layer 6 is greater than 50 μm, the photoreceptor may have poor resolution.

Additives for Photosensitive Layer

To improve sensitivity and suppress a residual potential increase and fatigue resulting from repeated use, at least one electron accepting material or a dye may be further added to the photosensitive layer 4.

Examples of the electron accepting material may include an electron attracting material, such as, an acid anhydride, including succinic anhydride, maleic anhydride, phthalic anhydride, and 4-chlorophthalic anhydride; a cyano compound, including tetracyanoethylene and terephthalic malonic dinitrile; an aldehyde, including 4-nitrobenzaldehyde; an anthraquinone, including anthraquinone and 1-nitroanthraquinone; a polycyclic or heterocyclic nitro compounds, including 2,4,7-trinitrofluorenone and 2,4,5,7-tetranitrofluorenone; and a diphenoquinone compound, and a polymerization product of at least one of these electron attracting materials.

Examples of the dye may include an organic photoconductive compound, for example, a xanthane-based dye, a thiazine dye, a triphenylmethane dye, a quinoline-based pigment, and copper phthalocyanine. These organic photoconductive compounds may be utilized as an optical sensitizer.

A protective layer may be formed on a surface of the photosensitive layer 4. The protective layer may improve the printing durability of the photosensitive layer 4 and may protect the photosensitive layer 4 from chemical attack of ozone or nitrogen oxides generated during charging of surfaces of the photoreceptor by corona discharge. The protective layer may include, for example, a resin, an inorganic filler-containing resin, or an inorganic oxide.

Intermediate Layer

Figure 2:
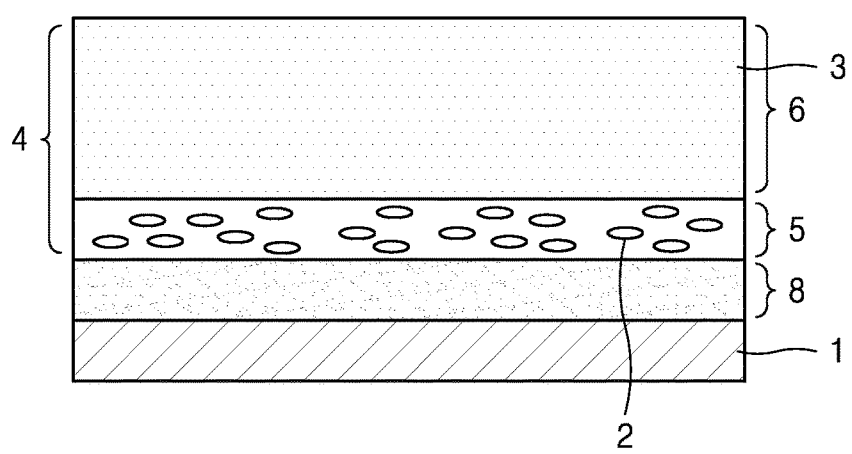
FIG. 2 is a schematic cross-sectional view illustrating another embodiment of an electrophotographic photoreceptor according to the present disclosure.

FIG. 2 is a schematic cross-sectional view illustrating a structure of an electrophotographic photoreceptor according to another embodiment of the present disclosure. Referring to FIG. 2, the electrophotographic photoreceptor of FIG. 2 is similar to the electrophotographic photoreceptor of FIG. 1, and thus, elements equivalent to those in FIG. 1 are denoted by the same reference numerals as used in FIG. 1. Thus the descriptions thereof will be omitted. However, there is a difference between the electrophotographic photoreceptor of FIG. 1 and the electrophotographic photoreceptor of FIG. 2 in that the electrophotographic photoreceptor of FIG. 2 may further include an intermediate layer 8 between the electrically conductive substrate 1 and the photosensitive layer 4.

When the intermediate layer 8 is not between the electrically conductive substrate 1 and the photosensitive layer 4, the charging characteristics of the photosensitive layer 4 may be deteriorated due to the injection of charges from the electrically conductive substrate 1 to the photosensitive layer 4. Accordingly, the surface charges of the photosensitive layer 4, excluding the surface charges on an area to be erased through exposure, may be reduced, which causes image defects, such as fogging of images. When forming an image by using a phase inversion development process in which a toner image forms on the portion of which surface charges have been reduced through exposure to light, if surface charges have been reduced through a cause other than exposure to light, fogging of images due to fine black dots resulting from toner adhesion to a white medium may occur, causing serious image quality deterioration. That is, a defect of the electrically conductive substrate 1 or the photosensitive layer 4 may deteriorate the charging characteristics in a small area of the electrically conductive substrate 1 or the photosensitive layer 4, and consequently cause fogging of images and serious image defects.

As described above, the inclusion of the intermediate layer 8 may prevent charges from the electrically conductive substrate 1 from injecting into the photosensitive layer 4, thus preventing deterioration of the charging characteristics of the photosensitive layer 4 and may also suppress the reduction of surface charges, excluding the surface charges on an area to be erased through exposure, thus preventing image defects, such as image fogging.

The intermediate layer 8 may cover surface defects on the electrically conductive substrate 1, thereby improving the smoothness of the electrically conductive substrate 1 and the film formability of the photosensitive layer 4. The intermediate layer 8 may also suppress separation of the photosensitive layer 4 from the electrically conductive substrate 1, thereby improving the adhesion between the electrically conductive substrate 1 and the photosensitive layer 4.

The intermediate layer 8 may be a resin layer including any of a variety of resin materials or an alumite layer. Examples of the resin materials may include a resin, such as polyethylene, polypropylene, polystyrene, an acrylic resin, vinyl chloride resin, vinyl acetate resin, polyurethane, an epoxy resin, polyester, a melamine resin, a silicone resin, polyvinyl butyral, and polyamide, a copolymer resin, including at least two repeating units of the foregoing resins, casein, gelatin, polyvinyl alcohol, and ethyl cellulose.

In some embodiments, the intermediate layer 8 may be a layer including a polyamide resin, and in some embodiments, the intermediate layer 8 may be a layer including an alcohol-soluble nylon resin. Examples of the alcohol-soluble nylon resin may include a copolymerized nylon obtained by copolymerization of, for example, nylon-6, nylon-6,6, nylon-6,10, nylon-11, and nylon-2; and a chemically-modified nylon resin, for example, N-alkoxymethylated nylon and N-alkoxyethylated nylon.

The intermediate layer 8 may include particles, such as metal oxides particles. Due to the inclusion of the particles, the intermediate layer 8 may adjust a volume resistance thereof and further prevent the charges from the electrically conductive substrate 1 from injecting into the photosensitive layer 4 and at the same time maintain electrical characteristics of the photoreceptor under various environmental conditions. Examples of the metal oxide particles may include titanium oxide particles, aluminum oxide particles, aluminum hydroxide particles, and tin oxide particles.

When the intermediate layer 8 includes the metal oxide particles, the intermediate layer 8 may be formed by coating an intermediate layer coating solution that may be prepared by dispersing the metal oxide particles in a resin solution including the foregoing resins, onto the electrically conductive substrate 1. Examples of a solvent for the resin solution may include water or various organic solvents. In some embodiments, the solvent for the resin solution may be a single solvent, such as water, methanol, ethanol, or butanol; a mixed solvent of water and an alcohol, a mixed solvent of at least two alcohols, a mixed solvent of an alcohol and acetone or dioxolane, and a mixed solvent of an alcohol and a chlorinated solvent, such as dichloroethane, chloroform, and trichloroethane.

The dispersing of the metal oxide particles in the resin solution may be performed by any conventional method using a ball mill, a sand mill, an attritor, a vibration mill, or an ultrasonic dispersing device.

A ratio (C:D) of the total amount (C) of the resin and the metal oxide particles in the intermediate layer coating solution to an amount (D) of the solvent in the intermediate layer coating solution may be in a range of about 1:99 to about 40:60 by mass %, and in some embodiments, about 2:98 to about 30:70 by mass %. A ratio of the resin to the metal oxide particles may be in a range of about 90:10 to about 1:99 by mass %, and in some embodiments, about 70:30 to about 5:95 by mass %.

A method of coating the intermediate layer coating solution may be, for example, a spray coating method, a bar coating method, a roll coating method, a blade method, a ring method, or a dip coating method. As described above, the dip coating method is relatively simple and advantageous in terms of productivity and costs, and thus is mainly used to form the intermediate layer 8.

The intermediate layer 8 may have a thickness of about 0.01 μm to about 20 μm, and in some embodiments, about 0.05 μm to about 10 μm. When the thickness of the intermediate layer 8 is smaller than about 0.01 μm, the intermediate layer 8 may substantially not function properly. Accordingly, the intermediate layer 8 may not coat surface defects on the electrically conductive substrate 1, thus failing to provide a uniformly smooth surface of the electrically conductive substrate 1 and prevent charges from the electrically conductive substrate 1 from injecting into the photosensitive layer 4, and thus, the charging characteristics of the photosensitive layer 4 may be deteriorated.

When the thickness of the intermediate layer 8 is greater than about 20 μm, the workability of forming the intermediate layer 8 by a dip coating method may decrease, and the photosensitive layer 4 may not be uniformly formed on the intermediate layer 8, thereby making the sensitivity of the photoreceptor prone to decrease.

Single-Layered Electrophotographic Photoreceptor

Figure 3:
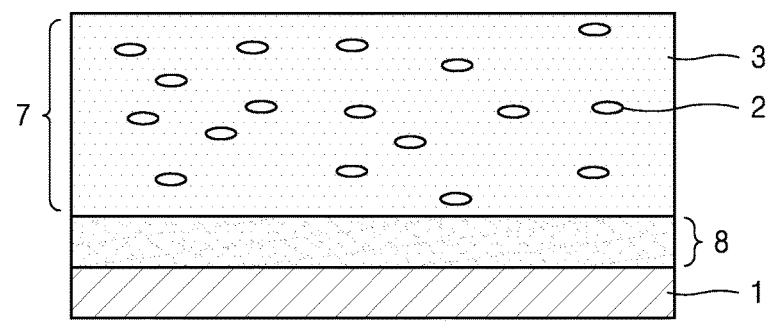
FIG. 3 is a schematic cross-sectional view illustrating another embodiment of an electrophotographic photoreceptor according to the present disclosure.

FIG. 3 is a schematic cross-sectional view illustrating a structure of an electrophotographic photoreceptor according to another embodiment of the present disclosure. Referring to FIG. 3, the electrophotographic photoreceptor of FIG. 3 is similar to the electrophotographic photoreceptor of FIG. 2, and thus, elements equivalent to those in FIG. 2 are denoted by the same reference numerals as used in FIG. 2. Thus the descriptions thereof will be omitted. Unlike the electrophotographic photoreceptor of FIG. 2, the electrophotographic photoreceptor of FIG. 3 is a single-layered electrophotographic photoreceptor including a photosensitive layer 7 that has a single-layered structure including the charge generating material 2 and the charge transporting material 3 along with a binder resin in the same layer.

The photosensitive layer 7 may be formed in the same manner as the charge transporting layer 6 of the previous embodiment of FIG. 2. For example, the charge generating material 2, the charge transporting material 3 including at least one organic photoconductive material of at least one of Formulae (1) and (1'), and a binder resin may be dissolved or dispersed in an appropriate solvent to prepare a photosensitive layer coating solution. The photosensitive layer coating solution may be coated on the intermediate layer 8 by a dip coating method to form a photosensitive layer 7.

A mass ratio of the charge transporting material 3 to the binder resin in the photosensitive layer 7 may be the same as the above-described ratio (A:B) of the charge transporting material 3 to the binder resin in the charge transporting layer 6, for example, about 10:12 to about 10:30.

The photosensitive layer 7 may have a thickness of about 5 μm to about 100 μm, and in some embodiments, about 10 μm to about 50 μm. When the thickness of the photosensitive layer 7 is less than about 5 μm, the photoreceptor may have poor surface charge retainability. When the thickness of the photosensitive layer 7 is greater than about 100 μm, productivity of preparing the photosensitive layer 7 may be lowered.

The electrophotographic photoreceptor may have any of a variety of layered structures, and is not limited to the structures of FIGS. 1 to 3.

Each of the layers of the electrophotographic photoreceptor may further include any of a variety of additives, such as, an antioxidant, a sensitizer, and an ultraviolet ray absorbent, if necessary. This may improve potential characteristics as well as stability of a coating solution when a layer is formed by coating, and may suppress fatigue deterioration resulting from repeated use of the electrophotographic photoreceptor, thereby improving the durability of the electrophotographic photoreceptor.

Examples of the antioxidant may include a phenolic compound, a hydroquinone-based compound, a tocopherol-based compound, and an amine-based compound. The amount of the antioxidant may be in a range of about 0.1 mass % to about 50 mass % based on the amount of the charge transporting material 3. When the amount of the antioxidant is less than 0.1 mass %, satisfactory improvements may not be achieved in the stability of the coating solution and the durability of the electrophotographic photoreceptor. When the amount of the antioxidant is greater than 50 mass %, the characteristics of the electrophotographic photoreceptor may be deteriorated.

Hereinafter, an electrophotographic imaging apparatus including an electrophotographic photoreceptor according to one or more embodiments will be described. However an electrophotographic imaging apparatus according to the present disclosure is not limited to the following description.

Figure 4:
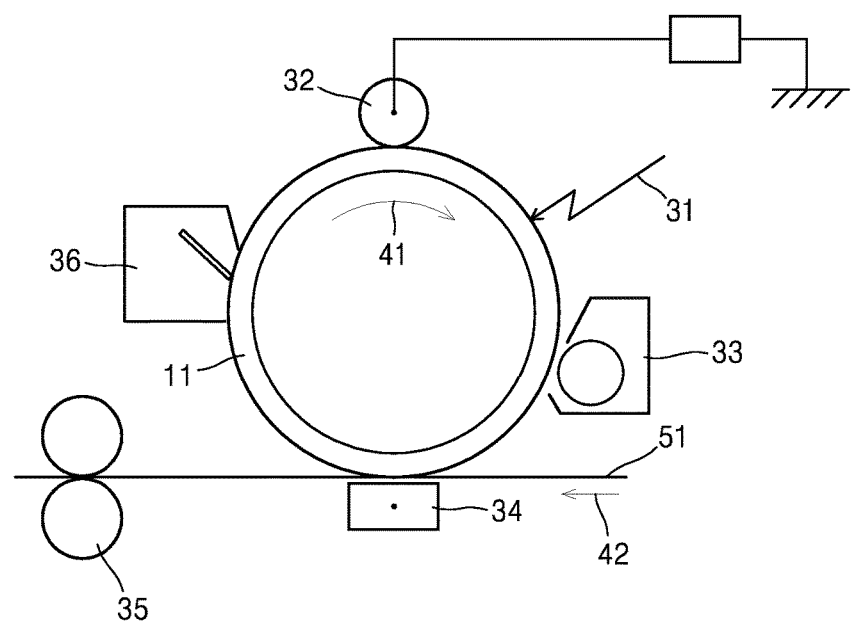
FIG. 4 is a schematic cross-sectional view illustrating an embodiment of an electrophotographic imaging apparatus according to the present disclosure, which includes an electrophotographic photoreceptor according to the present disclosure.

FIG. 4 is a schematic cross-sectional view illustrating a structure of an electrophotographic imaging apparatus that includes an electrophotographic photoreceptor according to an embodiment of the present disclosure.

The electrophotographic imaging apparatus of FIG. 4 may include an electrophotographic photoreceptor 11 according to an embodiment of the present disclosure. The electrophotographic photoreceptor 11, which has a cylindrical shape, may be rotated with a specific circumferential velocity in a direction indicated by reference numeral 41 by a driving unit (not shown). A charger 32, a semiconductor laser (not shown), a developer 33, a transfer charger 34, and a cleaner 36 may be sequentially disposed around the electrophotographic photoreceptor 11 along the rotation direction of the electrophotographic photoreceptor 11. A fixing unit 35 may be installed in a forward direction of a transfer medium 51.

An imaging process of the electrophotographic imaging apparatus will be described in detail. First, a surface of the electrophotographic photoreceptor 11 may be uniformly charged with a predetermined positive or negative potential by the charger 32 that may be a contact-type or non-contact type. Then the surface of the electrophotographic photoreceptor 11 may be exposed to a laser beam 31 radiated from the semiconductor laser (not shown). The laser beam 31 may repeatedly scan the surface of the electrophotographic photoreceptor 11 in a main scanning direction, i.e., a longitudinal direction of the electrophotographic photoreceptor 11, to form an electrostatic latent image on the surface of the electrophotographic photoreceptor 11. The electrostatic latent image may be developed into a toner image by the developer 33 that is provided downstream of the laser beam 31 along the rotation direction of the electrophotographic photoreceptor 11.

In synchronization with the exposure of the electrophotographic photoreceptor 11, the transfer medium 51 may be moved in a direction indicated by reference number 42 toward the transfer charger 34 that is provided downstream of the developer 33. The toner image formed on the surface of the electrophotographic photoreceptor 11 by the developer 33 may be transferred onto a surface of the transfer medium 51 by the transfer charger 34. The transfer medium 51 with the transferred toner image thereon may be moved to the fixing unit 35 by a conveyer belt (not shown), and the toner image may be fixed onto the transfer medium 51 by the fixing unit 35 to form a part of the final image.

The toner remaining on the surface of the electrophotographic photoreceptor 11 may be removed by an erasing lamp (not shown) and a cleaner 36 that are provided in a downward rotation direction of the transfer charger 34 and an upward rotation direction of the charger 32. These imaging processes may be repeated by the continuous rotation of the electrophotographic photoreceptor 11, forming a final image on the transfer medium 51. The transfer medium 51 with the final image thereon may be discharged out of the imaging apparatus.

In some embodiments, an electrophotographic photoreceptor of an imaging apparatus may include at least one organic photoconductive material of Formulae (1) and (1') as a charge transporting material, as described above. Thus, the electrophotographic photoreceptor may have a high charge potential, a sufficient photoresponsive property with high sensitivity, and a high durability. Moreover, these properties may be all maintained even when the electrophotographic photoreceptor is used in low-temperature environments or high-speed processes.

Accordingly, a highly reliable imaging apparatus that may provide high quality images in various environments may be obtained. The characteristics of the electrophotographic photoreceptor may not deteriorate even in the case of exposure to light. Accordingly, the image quality of the electrophotographic imaging apparatus may be maintained even when, for example, the electrophotographic photoreceptor is exposed to light during a maintenance process, thereby improving the reliability of the imaging apparatus.

MODE OF THE INVENTION

One or more embodiments of the present disclosure will now be described in detail with reference to the following examples. However, these examples are for illustrative purposes only and are not intended to limit the scope of the one or more embodiments of the present disclosure.

Preparation Example 1

Preparation of exemplary compound 1

Preparation Example 1-1

Preparation of Butadiene-Based Intermediate (A)

2.5 g (1.1 equivalents) of potassium t-butoxide was suspended in 50 mL of anhydrous tetrahydrofuran (THF) at 0° C. (in ice) to obtain a suspension. This suspension was slowly added dropwise to a solution of 5.0 g (1.0 equivalent) of a Wittig reagent represented by Formula (5) in 30 mL of anhydrous THF, to produce a reaction active species solution:

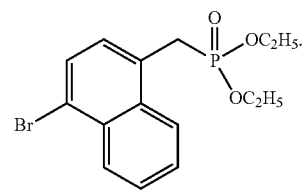

(5)

The reaction active species solution was slowly added dropwise to a solution of 5.24 g (1.0 equivalent) of 4-iodo-cinnamoyl aldehyde in 30 mL of anhydrous THF at 0° C. (in ice), stirred at 0° C. (in ice) for about 30 minutes, and then heated to about 40° C. to about 50° C. to terminate reaction. Once the reaction was complete, concentrating of THF, extracting with a separatory funnel within water and ethyl acetate, and drying and concentrating an extracted organic layer were carried out to obtain a crude product using a conventional method. This crude product was recrystallized using a mixed solvent of methanol and ethyl acetate to obtain about 8.7 g of a powder-form compound.

The obtained powder-form compound was analyzed using liquid chromatography-mass spectrometry (LC-MS). As a result, the compound was identified as a butadiene-based intermediate (A) represented by Formula (7) with different halogen atoms substituted at specific sites, which had a calculated molecular weight of 461.14 and exhibited a peak of proton-added molecular ions [M+H]+ at about 462.5 (Yield: 85%):

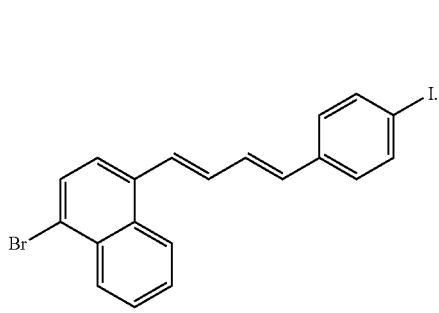

(7)

As a result of the LC-MS analysis, it was found that the butadiene-based intermediate (A) had a purity of 99.3%.

Preparation Example 1-2

Preparation of Amine Intermediate (B)

2.25 g (0.95 equivalents) of bis(p-tolyl) amine, 5.0 g (1.0 equivalent) of the butadiene-based intermediate (A), and 1.04 g (0.95 equivalents) of sodium t-butoxide were mixed in 80 mL of toluene to obtain a toluene solution. Separately, 0.02 g of palladium acetate and 0.08 g of a phosphine compound represented by Formula (13) were added to 5 mL of THF and dissolved with stirring to obtain a solution. Then, this solution was added to the toluene solution:

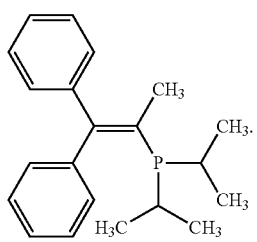

(13)

The mixture solution was heated with stirring at about 60° C. for about 16 hours in a nitrogen atmosphere to obtain a mixture. After the mixture was cooled to room temperature, 50 mL of hot water and 80 mL of toluene were added to the mixture, stirred, and filtered using a Celite filter. Thereafter, an organic layer was obtained therefrom by means of stationary decanting. The organic layer was further washed with 80 mL of hot water, concentrated, and then recrystallized using a mixed solvent of toluene and heptane to obtain 4.02 g of a powder-form compound.

The powder-form compound was analyzed using LC-MS. As a result, the compound was identified as an amine intermediate (B) represented by Formula (14), which had a calculated molecular weight of 530.51 and exhibited a peak of proton-added molecular ions [M+1-1]+ at 531.6 (Yield: 70%):

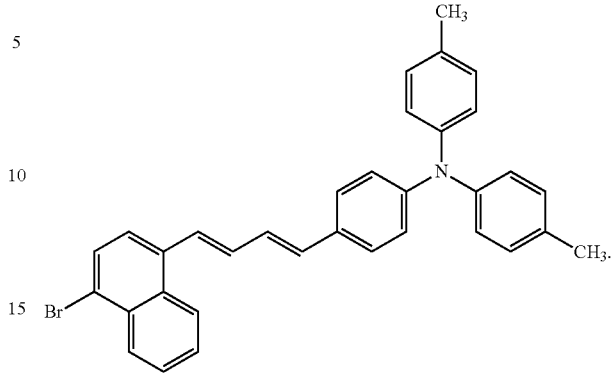

(14)

As a result of the LC-MS analysis, it was found that the amine intermediate (B) of Formula (14) had a purity of 98.5%.

Preparation Example 1-3

Preparation of Diamine Intermediate (C)

0.67 g (0.95 equivalents) of p-anisidine, 2.6 g (1.0 equivalent) of amine intermediate (B), and 0.52 g (0.95 equivalent) of sodium t-butoxide were mixed in 40 mL of toluene to obtain a toluene solution. Separately, 0.01 g of palladium acetate and 0.04 g of the phosphine compound represented by Formula (13):

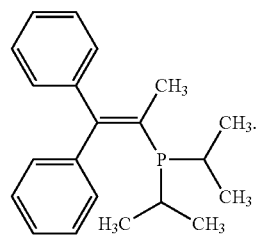

(13)

were added to 5 mL of THF and dissolved with stirring to obtain a solution. Then, this solution was added to the toluene solution. The mixture solution was heated with stirring at about 80° C. for about 16 hours in a nitrogen atmosphere to obtain a mixture. After the mixture was cooled to room temperature, 30 mL of hot water and 60 mL of toluene were added to the mixture, stirred, and filtered using a Celite filter. Thereafter, an organic layer was obtained therefrom by means of stationary decanting. The organic layer was further washed with 60 mL of hot water, concentrated, and then recrystallized using a mixed solvent of toluene and heptane to obtain 2.4 g of a pale-yellow-color compound.

The powder-form compound was analyzed using LC-MS. As a result, the compound was identified as an amine intermediate (C) represented by Formula (15), which had a calculated molecular weight of 572.76 and exhibited a peak of proton-added molecular ions [M+H]+ at 573.8 (Yield: 85%):

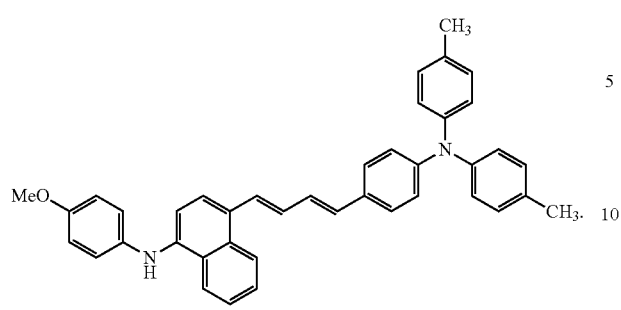

(15)

As a result of the LC-MS analysis, it was found that the amine intermediate (C) of Formula (15) had a purity of 98.3%.

Preparation Example 1-4

Preparation of Exemplary Compound 1

After 2.0 g (1.0 equivalents) of diamine intermediate (C), 0.72 g (1.05 equivalents) of diphenyl acetaldehyde, and 0.01 g of DL-10-camphorsulfonic acid as an acid catalyst were added to 50 mL of toluene and then heated for reaction for 6 hours while a resulting byproduct water was azeotropically removed with toluene. Once the reaction was complete, the reaction solution was concentrated to one tenth (1/10), and then slowly added dropwise to 100 mL of hexane with vigorous stirring to generate crystals. The resulting crystals were separated by filtration, and then recrystallized in a mixed solvent of ethanol and ethyl acetate to obtain 2.5 g of a powder-form compound in yellow color.

The obtained powder-form compound was analyzed using LC-MS. As a result, the compound was identified as an asymmetric butadiene-based compound (exemplary compound 1) represented by Formula (4), which had a calculated molecular weight of 750.99 and exhibited a peak of proton-added molecular ions [M+H]+ at 752.1 (Yield: 95%):

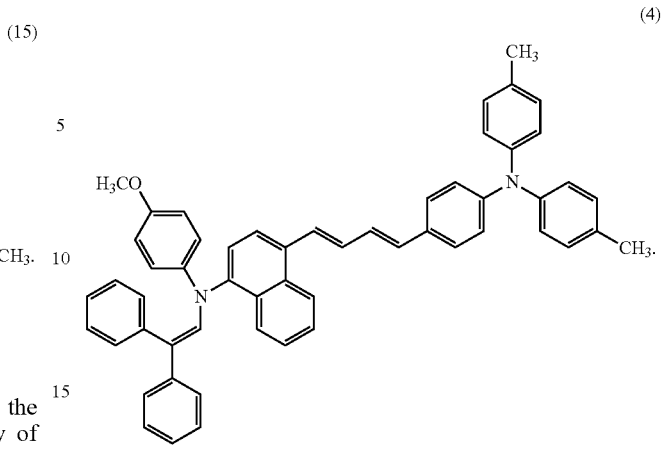

(4)

As a result of the LC-MS analysis, the asymmetric butadiene-based compound (exemplary compound 1) of Formula (4) had a purity of 99.5%.

Exemplary compounds 2 to 40 in Tables 1 and 2 may be synthesized by controlling the reactivity of the butadiene-based intermediate (A) with different halogen atoms substituted at specific positions and the reaction conditions used in Preparation Examples 1-1 to 1-4 to induce selective substitution of iodine atoms with various secondary aryl amine derivatives (First Stage), substitution of bromine atoms with various primary aryl amine derivative (Second Stage), and then enamination of the resulting compounds with various acetaldehyde derivatives (Final Stage). Although the yields in each of the reaction stages may slightly be different depending on substitution sites and types of substituents of source materials (i.e., secondary aryl amine derivatives, primary aryl amine derivative, and acetaldehyde derivatives), the yield may fall within the range of yields in Preparation Examples 1-1 to 1-4, without a significant reduction.

Purities, calculated molecular weights, and peaks for molecular ions [M+H]+ of the final synthesized compounds used in the following examples are shown in Table 3A.

TABLE 3A

| Exemplary Compound No. 1 | Structural Formula | LC-MS Purity (%) | Calculated Molecular Weight | Peak for LC-MS molecular ions [M + H]+ |
|---|---|---|---|---|
| 1 |  | 99.5 | 750.99 | 751.4 |

TABLE 3A-continued
| Exemplary Compound No. 1 | Structural Formula | LC-MS Purity (%) | Calculated Molecular Weight | Peak for LC-MS molecular ions [M + H]+ |
| --- | --- | --- | --- | --- |
| 3 | | 98.3 | 752.96 | 753.6 |
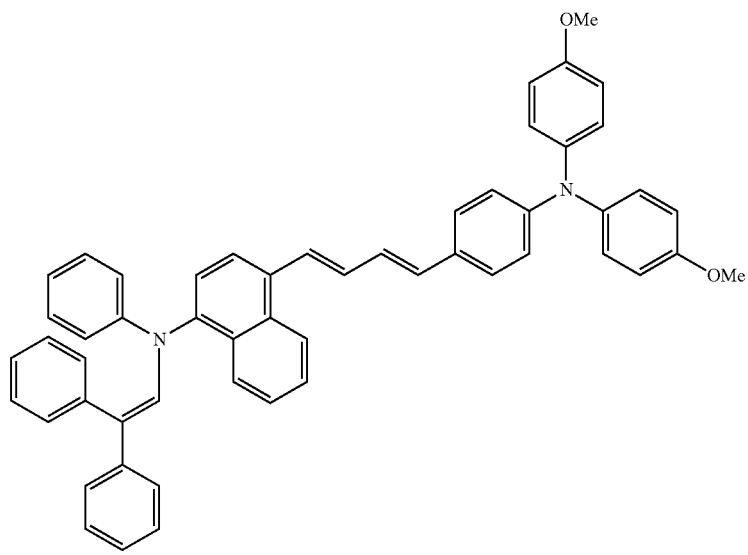 [SMILES: COc1ccc(N(c2ccc(/C=C/C=C/c3ccc(N(C=C(c4ccccc4)c4ccccc4)c4ccccc4)c4ccccc34)cc2)c2ccc(OC)cc2)cc1]
| 4 | | 98.6 | 763.05 | 763.7 |
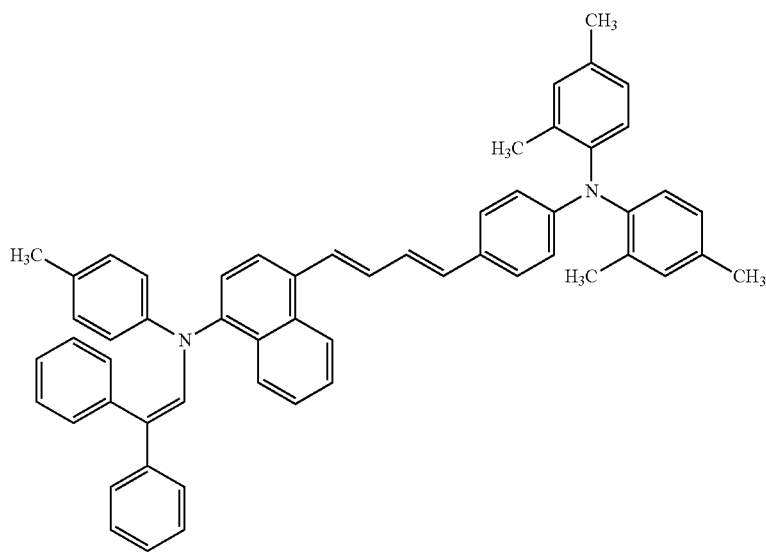

TABLE 3A-continued
| Exemplary Compound No. 1 | Structural Formula | LC-MS Purity (%) | Calculated Molecular Weight | Peak for LC-MS molecular ions [M + H]+ |
| --- | --- | --- | --- | --- |
| 12 | | 99.2 | 734.99 | 735.7 |
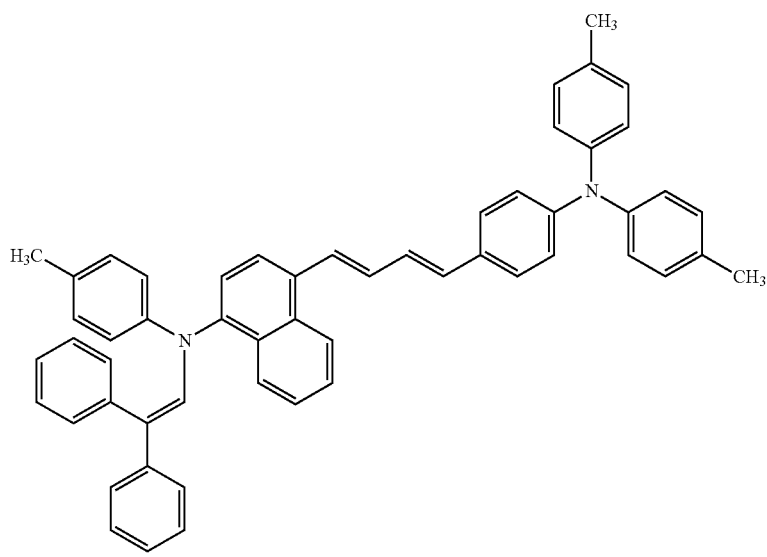
| 21 | | 98.7 | 720.97 | 721.8 |
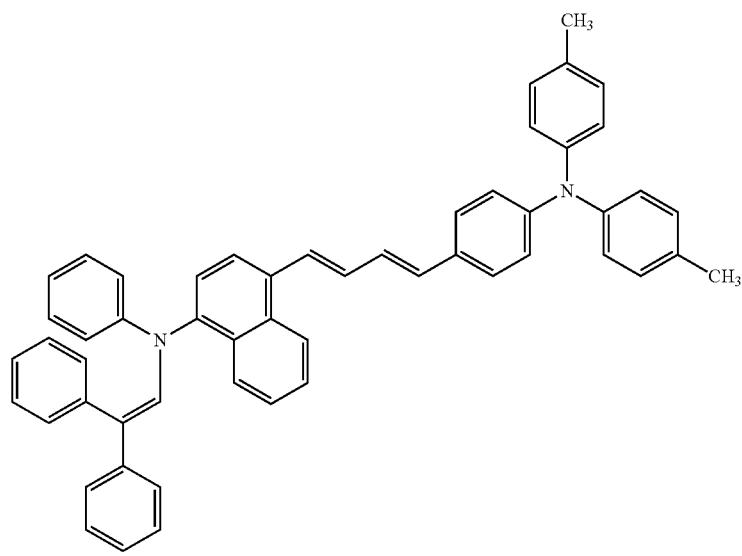 [SMILES: Cc1ccc(N(c2ccc(C)cc2)c2ccc(/C=C/C=C/c3ccc(N(C=C(c4ccccc4)c4ccccc4)c4ccccc4)c4ccccc34)cc2)cc1]

TABLE 3A-continued

| Exemplary Compound No. 1 | Structural Formula | LC-MS Purity (%) | Calculated Molecular Weight | Peak for LC-MS molecular ions [M + H]+ |
|---|---|---|---|---|
| 23 | | 99.3 | 779.05 | 779.6 |

Preparation Example 2

Preparation of Exemplary Compound 1'

Preparation Example 2-1

Preparation of Butadiene-Based Intermediate (A')

1.65 g (1.1 equivalents) of potassium t-butoxide was suspended in 50 mL of anhydrous THF at 0° C. (in ice) to obtain a suspension. This suspension was slowly added dropwise to a solution of 5.0 g (1.0 equivalent) of a Wittig reagent represented by Formula (5') in 30 mL of anhydrous THF, to produce a reaction active species solution:

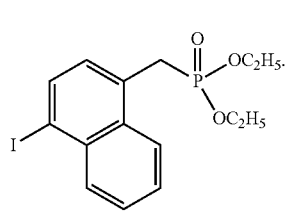

(5')

The reaction active species solution was slowly added dropwise to a solution of 2.83 g (1.0 equivalent) of 4-bromocinnamoyl aldehyde in 30 mL of anhydrous THF at 0° C. (in ice), stirred at 0° C. (in ice) for 30 minutes, and then heated to 40° C. to 50° C. to terminate reaction. Once the reaction was complete, concentrating of THF, extracting with a separatory funnel within water and ethyl acetate, and drying and concentrating an extracted organic layer were carried out to obtain a crude product using a conventional method. This crude product was recrystallized using a mixed solvent of methanol and ethyl acetate to obtain 5.76 g of a powder-form compound.

The obtained powder-form compound was analyzed using LC-MS. As a result, the compound was identified as a butadiene-based intermediate (A') represented by Formula (7') with different halogen atoms substituted at specific sites, which had a calculated molecular weight of 461.14 and exhibited a peak of proton-added molecular ions [M+H]+ at 462.7 (Yield: 93.3%):

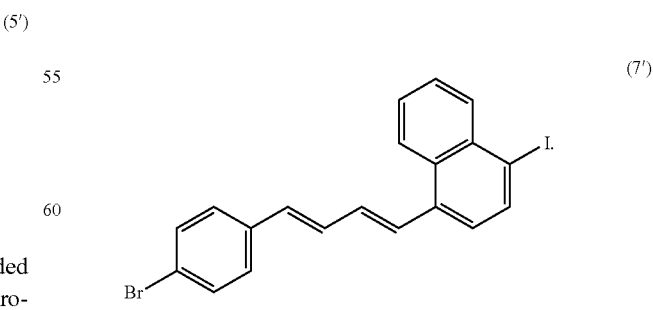

(7')

As a result of the LC-MS analysis, it was found that the butadiene-based intermediate (A') had a purity of 99.5%.

Preparation Example 2-2

Preparation of Amine Intermediate (B')

2.35 g (0.95 equivalents) of bis(p-tolyl) amine, 5.5 g (1.0 equivalent) of the butadiene-based intermediate (A'), and 1.04 g (0.95 equivalents) of sodium t-butoxide were mixed in 80 mL of toluene to obtain a toluene solution. Separately, 0.02 g of palladium acetate and 0.08 g of a phosphine compound represented by Formula (13) were added to 5 mL of THF and dissolved with stirring to obtain a solution. Then, this solution was added to the toluene solution:

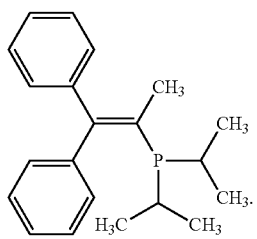

(13)

The mixture solution was heated with stirring at 60° C. for 16 hours in a nitrogen atmosphere to obtain a mixture. After the mixture was cooled to room temperature, 50 mL of hot water and 80 mL of toluene were added to the mixture, stirred, and filtered using a Celite filter. Thereafter, an organic layer was obtained therefrom by means of stationary decanting. The organic layer was further washed with 80 mL of hot water, concentrated, and then recrystallized using a mixed solvent of toluene and heptane to obtain 4.75 g of a powder-form compound.

The powder-form compound was analyzed using LC-MS. As a result, the compound was identified as an amine intermediate (B') represented by Formula (14'), which had a calculated molecular weight of 530.51 and exhibited a peak of proton-added molecular ions [M+H]+ at 531.8 (Yield: 75%):

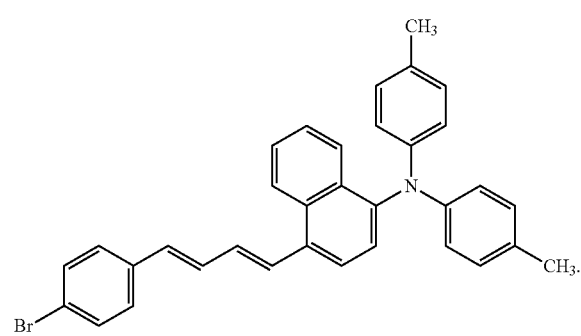

(14')

As a result of the LC-MS analysis, it was found that the amine intermediate (B') of Formula (14') had a purity of 99.1%.

Preparation Example 2-3

Preparation of Diamine Intermediate (C')

0.67 g (1.1 equivalents) of p-anisidine, 4.52 g (1.0 equivalent) of amine intermediate (B'), and 0.9 g (1.1 equivalent) of sodium t-butoxide were mixed in 40 mL of toluene to obtain a toluene solution. Separately, 0.01 g of palladium acetate and 0.04 g of a phosphine compound represented by Formula (13) were added to 5 mL of THF and dissolved with stirring to obtain a solution. Then, this solution was added to the toluene solution:

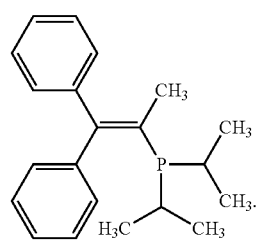

(13)

The mixture solution was heated with stirring at 80° C. for 16 hours in a nitrogen atmosphere to obtain a mixture. After the mixture was cooled to room temperature, 30 mL of hot water and 60 mL of toluene were added to the mixture, stirred, and filtered using a Celite filter. Thereafter, an organic layer was obtained therefrom by means of stationary decanting. The organic layer was further washed with 60 mL of hot water, concentrated, and then recrystallized using a mixed solvent of toluene and heptane to obtain 4.3 g of a pale-yellow-color compound.

The powder-form compound was analyzed using LC-MS. As a result, the compound was identified as a diamine intermediate (C') represented by Formula (15'), which had a calculated molecular weight of 572.76 and exhibited a peak of proton-added molecular ions [M+H]+ at 573.9 (Yield: 90%):

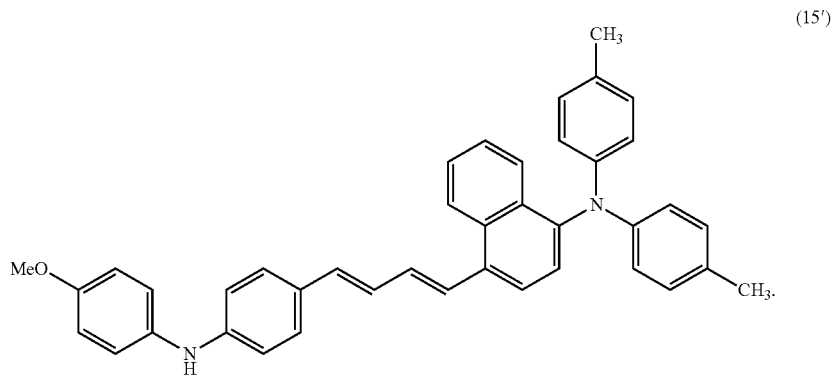 [SMILES: COc1ccc(Nc2ccc(/C=C/C=C/c3ccc(N(c4ccc(C)cc4)c4ccc(C)cc4)c4ccccc34)cc2)cc1]

(15')

As a result of the LC-MS analysis, it was found that the diamine intermediate (C') of Formula (15') had a purity of 98.8%.

Preparation Example 2-4

Preparation of Exemplary Compound 1'

2.0 g (1.0 equivalents) of diamine intermediate (C'), 0.72 g (1.05 equivalents) of diphenyl acetaldehyde, and 0.01 g of DL-10-camphorsulfonic acid as an acid catalyst were added to 50 mL of toluene, and then heated for reaction for 6 hours while a resulting byproduct water was azeotropically removed with toluene. Once the reaction was complete, the reaction solution was concentrated to one tenth (1/10), and then slowly added dropwise to 100 mL of hexane with vigorous stirring to generate crystals. The resulting crystals were separated by filtration, and then recrystallized in a mixed solvent of ethanol and ethyl acetate to obtain 2.49 g of a powder-form compound in yellow color.

The obtained powder-form compound was analyzed using LC-MS. As a result, the compound was identified as an asymmetric butadiene-based compound (exemplary compound 1') represented by Formula (4'), which had a calculated molecular weight of 750.99 and exhibited a peak of proton-added molecular ions [M+H]+ at 751.6 (Yield: 95%):

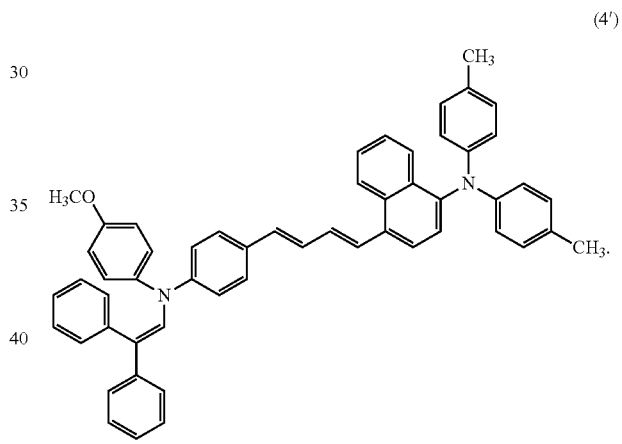

(4')

As a result of the LC-MS analysis, the asymmetric butadiene-based compound (exemplary compound 1') of Formula (4') had a purity of 99.6%.

Exemplary compounds 2' to 40' in Tables 1 and 2 may be synthesized by controlling the reactivity of the butadiene-based intermediate (A') with different halogen atoms substituted at specific positions and the reaction conditions used in Preparation Examples 2-1 to 2-4 to induce selective substitution of iodine atoms with various secondary aryl amine derivatives (First Stage), substitution of bromine atoms with various primary aryl amine derivative (Second Stage), and then enamination of the resulting compounds with various acetaldehyde derivatives (Final Stage). Although the yields in each of the reaction stages may slightly be different depending on substitution sites and types of substituents of source materials (i.e., secondary aryl amine derivatives, primary aryl amine derivative, and acetaldehyde derivatives), the yield may fall within the range of yields in Preparation Examples 2-1 to 2-4, without a significant reduction. Purities, calculated molecular weights, and peaks for molecular ions [M+H]+ of the final synthesized compounds used in the following examples are shown in Table 3B.

TABLE 3B

| Exemplary Compound No. 1 | Structural Formula | LC-MS Purity (%) | Calculated Molecular Weight | Peak for LC-MS molecular ions [M + H]+ |
|---|---|---|---|---|
| 1' | | 99.6 | 750.99 | 751.6 |
| 4' | | 99.4 | 763.05 | 764.3 |

TABLE 3B-continued
| Exemplary Compound No. 1 | Structural Formula | LC-MS Purity (%) | Calculated Molecular Weight | Peak for LC-MS molecular ions [M + H]+ |
|---|---|---|---|---|
| 9' | 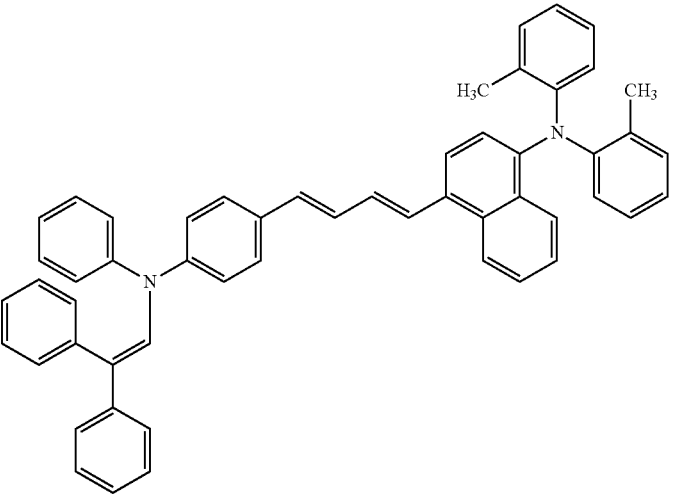 [SMILES: Cc1ccccc1N(c1ccccc1C)c1ccc(/C=C/C=C/c2ccc(N(C=C(c3ccccc3)c3ccccc3)c3ccccc3)cc2)c2ccccc12] | 98.7 | 720.97 | 721.8 |
| 14' | 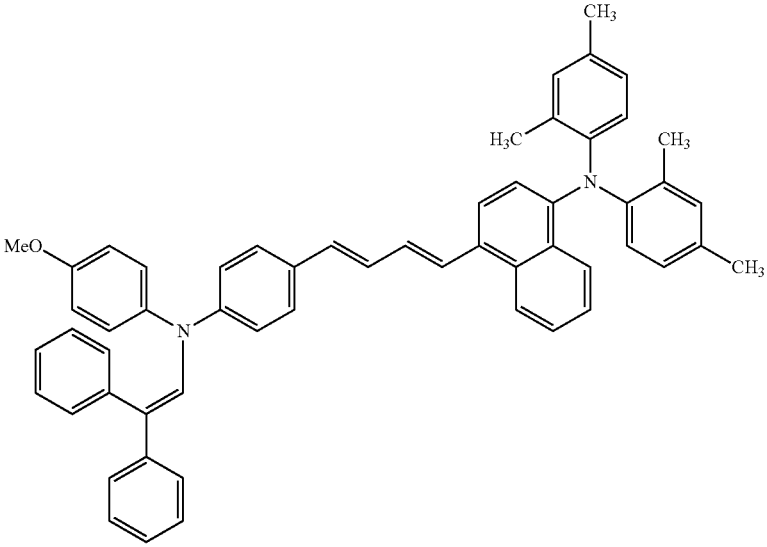 [SMILES: COc1ccc(N(C=C(c2ccccc2)c2ccccc2)c2ccc(/C=C/C=C/c3ccc(N(c4ccc(C)cc4C)c4ccc(C)cc4C)c4ccccc34)cc2)cc1] | 99.3 | 779.05 | 780.4 |
| 18' | 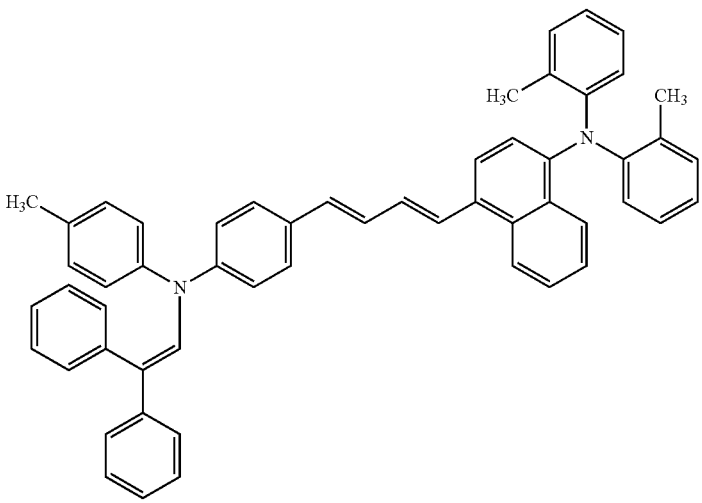 [SMILES: Cc1ccc(N(C=C(c2ccccc2)c2ccccc2)c2ccc(/C=C/C=C/c3ccc(N(c4ccccc4C)c4ccccc4C)c4ccccc34)cc2)cc1] | 99.2 | 734.99 | 735.8 |

TABLE 3B-continued

| Exemplary Compound No. 1 | Structural Formula | LC-MS Purity (%) | Calculated Molecular Weight | Peak for LC-MS molecular ions [M + H]+ |
|---|---|---|---|---|
| 26' | 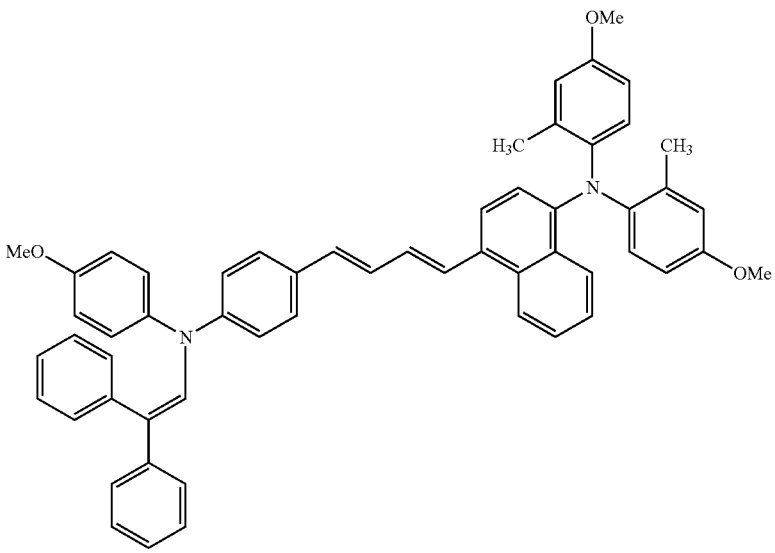 [SMILES: COc1ccc(N(C=C(c2ccccc2)c2ccccc2)c2ccc(/C=C/C=C/c3ccc(N(c4ccc(OC)cc4C)c4ccc(OC)cc4C)c4ccccc34)cc2)cc1] | 99.5 | 811.05 | 812.6 |

EXAMPLE 1A 1 part by mass of an azo compound represented by Formula (17) as the charge generating material 2 was added to a resin solution of 1 part by mass of phenoxy resin (available from Union Carbide Corporation, PKHH) dissolved in 99 parts by mass of THF. Then, the mixture solution was dispersed using a paint shaker for 2 hours to prepare 5 g of a charge generating layer coating solution:

The charge generating layer coating solution was coated on an aluminum-deposited surface of a polyester film having a thickness of 80 μm that served as an electrically conductive substrate 1, by using a Baker-type applicator and then dried to form the charge generating layer 5 having a thickness of 0.3 μm.

Next, 8 parts by mass of exemplary compound 1 in Table 1 which is an asymmetric butadiene-based compound as the charge transporting material 3 and 10 parts by mass of a polycarbonate resin (available from Teijin Ltd., TS-2040) as a binder resin were dissolved in 80 parts by mass of THF to prepare 5 g of a charge transporting layer coating solution.

(17)

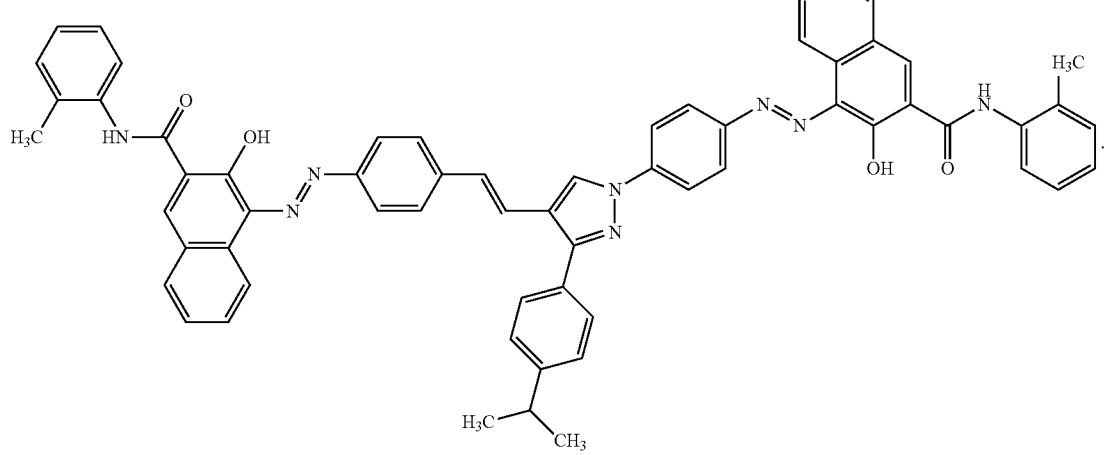

The charge transporting layer coating solution was coated on the charge generating layer 5 by using a Baker type applicator, and then dried to form a charge transporting layer 6 having a thickness of 20 μm.

Accordingly, it was complete to manufacture a laminated electrophotographic photoreceptor having a structure as illustrated in FIG. 1.

EXAMPLES 2A TO 6A

Electrophotographic photoreceptors were manufactured in the same manner as in Example 1A, except that exemplary compounds 3, 4, 12, 21, and 23 shown in Tables 1 and 2 were used in place of exemplary compound 1, which is an asymmetrical butadiene-based compound, as a charge transporting material 3, respectively.

EXAMPLES 1B TO 6B

Electrophotographic photoreceptors were manufactured in the same manner as in Example 1A, except that exemplary compounds 1', 4', 9', 14', 18', and 26' shown in Tables 3 and 4 were used in place of exemplary compound 1, which is an asymmetrical butadiene-based compound, as a charge transporting material 3, respectively.

COMPARATIVE EXAMPLE 1

An electrophotographic photoreceptor was manufactured in the same manner as in Example 1A, except that comparative compound (a) represented by Formula (18) was used in place of exemplary compound 1, which is an asymmetrical butadiene-based compound, as a charge transporting material 3:

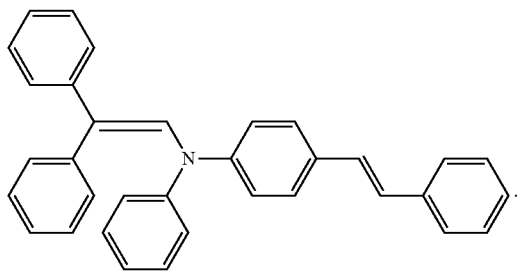

(18)

COMPARATIVE EXAMPLE 2

An electrophotographic photoreceptor was manufactured in the same manner as in Example 1A, except that compound (b) represented by Formula (19) was used in place of exemplary compound 1, which is an asymmetrical butadiene-based compound, as a charge transporting material 3:

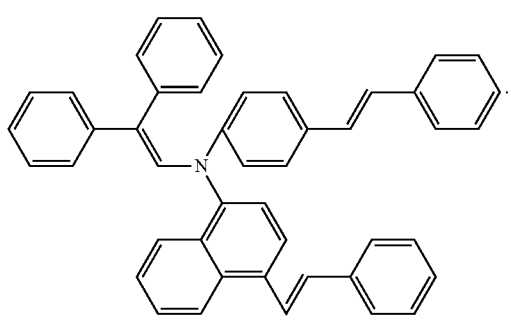

(19)

COMPARATIVE EXAMPLE 3

An electrophotographic photoreceptor was manufactured in the same manner as in Example 1A, except that compound (c) represented by Formula (20) was used in place of exemplary compound 1, which is an asymmetrical butadiene-based compound, as a charge transporting material 3:

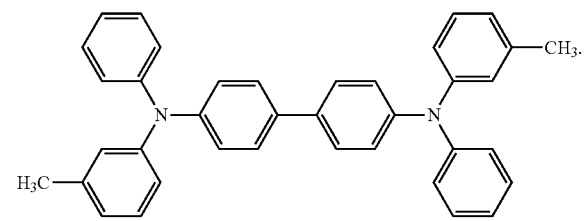

(20)

[Evaluation 1]

Ionization potentials of the surfaces of the electrophotographic photoreceptors of Examples 1A to 6A, Examples 1B to 6B, and Comparative Examples 1 to 3 were measured using a surface analysis instrument (AC-2, available from RIKEN KEIKI Co., Ltd.).

Gold was deposited on a surface of the photosensitive layer of each of the electrophotographic photoreceptors, and then a charge mobility of the charge transporting material 3 was measured at room temperature under a reduced pressure by using a time-of-flight method.

<Overall Evaluation>

Overall evaluation of the ionization potentials and the charge mobilities was performed according to the following criteria.

Very good (VG): a charge mobility of $1.0 \times 10^4$ cm$^2$/V/sec to $1.7 \times 10^4$ cm$^2$/V/sec Not bad (NB): a charge mobility of $1.0 \times 10^{-5}$ cm$^2$/V/sec to $5.0 \times 10^{-5}$ cm$^2$/V/sec Bad (B): a charge mobility of $8.5 \times 10^{-5}$ cm$^2$/V/sec to $9.5 \times 10^{-5}$ cm$^2$/V/sec.

The measurement and evaluation results are shown in Tables 4A and 4B. In Tables 4A and 4B, the numbers indicated for the charge transporting materials denotes the numbers for exemplary compounds.

TABLE 4A

| | | Charge Transporting Material | Ionization Potential (eV) | Charge Mobility (cm$^2$/V/sec) | Overall Evaluation |
|---|---|---|---|---|---|
| Examples | 1A | Compound (1) | 5.48 | $1.1 \times 10^{-4}$ | VG |
| | 2A | Compound (3) | 5.47 | $1.3 \times 10^{-4}$ | VG |
| | 3A | Compound (4) | 5.54 | $1.5 \times 10^{-4}$ | VG |
| | 4A | Compound (12) | 5.51 | $1.7 \times 10^{-4}$ | VG |
| | 5A | Compound (21) | 5.58 | $1.2 \times 10^{-4}$ | VG |
| | 6A | Compound (23) | 5.51 | $1.4 \times 10^{-4}$ | VG |
| Comparative Examples | 1 | Compound (a) | 5.62 | $1.7 \times 10^{-5}$ | NB |
| | 2 | Compound (b) | 5.63 | $8.5 \times 10^{-5}$ | B |
| | 3 | Compound (c) | 5.39 | $9.5 \times 10^{-5}$ | B |

TABLE 4B

| | | Charge Transporting Material | Ionization Potential (eV) | Charge Mobility (cm$^2$/V/sec) | Overall Evaluation |
|---|---|---|---|---|---|
| Examples | 1B | Compound (1') | 5.46 | $1.2 \times 10^{-4}$ | VG |
| | 2B | Compound (4') | 5.43 | $1.1 \times 10^{-4}$ | VG |

TABLE 4B-continued

| Charge Transporting Material | Ionization Potential (eV) | Charge Mobility (cm²/V/sec) | Overall Evaluation |
|---|---|---|---|
| 3B Compound (9') | 5.52 | 1.4 × 10⁻⁴ | VG |
| 4B Compound (14') | 5.48 | 1.6 × 10⁻⁴ | VG |

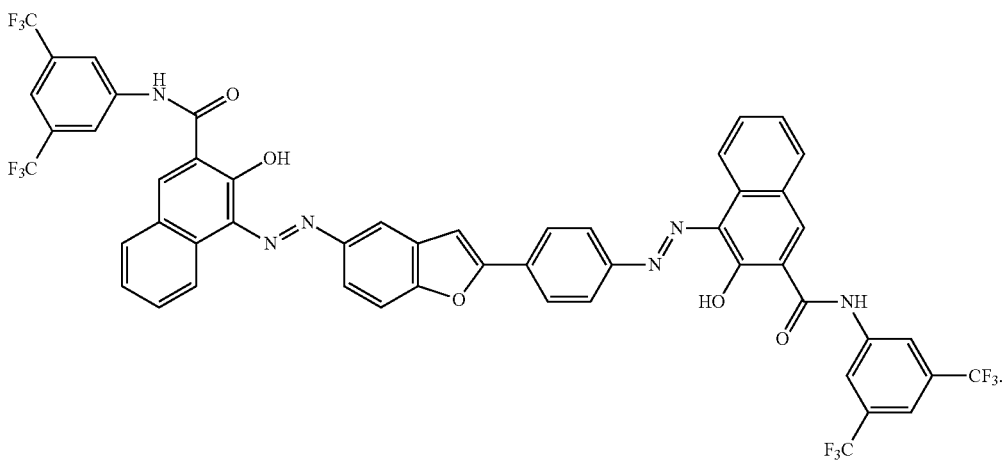

TABLE 4B-continued

| Charge Transporting Material | Ionization Potential (eV) | Charge Mobility (cm²/V/sec) | Overall Evaluation |
|---|---|---|---|
| 5B Compound (18') | 5.54 | 1.3 × 10⁻⁴ | VG |
| 6B Compound (26') | 5.49 | 1.5 × 10⁻⁴ | VG |

In Tables 4A and 4B, the charge mobilities were measured at an intensity of electric field of $2.5 \times 10^5$ V/cm.

From the above results of the electrophotographic photoreceptors of Examples 1A to 6A and 1B to 6B and Comparative Examples 1 to 3, using the asymmetrical butadiene-based compounds of at least one of Formulae (1) and (1') as charge transporting materials were found to have about one order-of-magnitude higher charge mobilities than using the conventional charge transporting materials, such as the enamine-styryl-based compound (a) or (b) or the triphenyl amine dimer-based (TPD) compound (c).

EXAMPLE 7A 9 parts by mass of dendritic titanium oxide (available from ISHIHARA SANGYO KAISHA LTD., TTO-D-1) surface-treated with aluminum oxide ($Al_2O_3$) and zirconium dioxide ($ZrO_2$), and 9 parts by mass of copolymerized nylon resin (available from TORAY INDUSTRIES INC., CM8000) were added to a mixture solvent of 41 parts by mass of 1,3-dioxolane and 41 parts by mass of methanol, and then dispersed using a paint shaker for 12 hours to prepare 5 g of an intermediate layer coating solution. The intermediate layer coating solution was coated on an aluminum substrate having a thickness of 0.2 mm, which serves as an electrically conductive substrate 1, by using a Baker type applicator, and then dried to form an intermediate layer 8 having a thickness of 1 μm.

Next, 2 parts by mass of an azo compound of Formula (21) (as a charge generating material 2) was added to a resin solution of 1 parts by mass of a polyvinyl butyral resin (available from SEKISUI CHEMICAL CO., LTD., BX-1) dissolved in 97 parts by mass of THF, and then dispersed using a paint shaker for 10 hours to prepare 5 g of a charge generating layer coating solution. The charge generating layer coating solution was coated on the intermediate layer 8 by using the Baker type applicator and then dried to form the charge generating layer 5 having a thickness of 0.3 μm:

(21)

Subsequently, 10 parts by mass of exemplary compound 1 in Table 1, as an asymmetric butadiene-based compound used as the charge transporting material 3, 14 parts by mass of a polycarbonate resin (available from TEIJIN LTD., TS-2040) as a binder resin, and 0.2 parts by mass of 2,6-di-t-butyl-4-methyl phenol were dissolved in 80 parts by mass of THF to prepare 5 g of a charge transporting layer coating solution. The charge transporting layer coating solution was coated on the charge generating layer 5 by using the Baker type applicator and then dried to form a charge transporting layer 6 having a thickness of 18 μm, thereby completing the manufacture of a laminated electrophotographic photoreceptor having a structure as illustrated in FIG. 2.

EXAMPLES 8A TO 12A

Electrophotographic photoreceptors were prepared in the same manner as in Example 7A, except that exemplary compounds 3, 4, 12, 21, and 28 in Tables 1 and 2, which are an asymmetric butadiene-based compound, were used in place of exemplary compound 1, which is an asymmetric butadiene-based compound, as a charge transporting material 3, respectively.

EXAMPLES 7B TO 12B

Electrophotographic photoreceptors were manufactured in the same manner as in Example 7A, except that exemplary compounds 1', 4', 9', 14', 18', and 26' shown in Tables 3 and 4 were used in place of exemplary compound 1, which is an asymmetrical butadiene-based compound, as a charge transporting material 3, respectively.

COMPARATIVE EXAMPLEs 4 AND 5

Electrophotographic photoreceptors were prepared in the same manner as in Example 7A, except that comparative compound (a) represented by Formula (18) above and comparative compound (c) represented by Formula (20) above were used in place of exemplary compound 1, which is an asymmetric butadiene-based compound, as a charge transporting material 3, respectively.

EXAMPLE 13A

After an intermediate layer coating solution was prepared in the same manner as in Example 7A, the intermediate layer coating solution was coated on an aluminum substrate having a thickness of 0.2 mm used as an electrically conductive substrate 1 and then dried to form an intermediate layer 8 having a thickness of 1 μm.

Next, 1 part by mass of the azo compound of Formula (21) above as the charge generating material 2, 12 parts by mass of a polycarbonate resin (TEIJIN LTD., TS-2040) as a binder resin, 10 parts by mass of exemplary compound 1 in Table 1 as an asymmetric butadiene-based compound used as a charge transporting material, 5 parts by mass of 3,5-dimethyl-3',5'-di-t-butyldiphenoquinone, and 0.5 parts by mass of 2,6-di-t-butyl-4-methylphenol were mixed in 65 parts by mass of THF for 12 hours by using a ball mill to prepare 5 g of a photosensitive layer coating solution. The photosensitive layer coating solution was coated on the intermediate layer 8 by using a Baker type applicator, and then dried using hot air at 130° C. for 1 hour to form a photosensitive layer 7 having a thickness of 20 μm, thereby completing the manufacture of a single-layered electrophotographic photoreceptor having a structure as illustrate in FIG. 3.

EXAMPLE 14A

An electrophotographic photoreceptor was prepared in the same manner as in Example 7A, except that an X-type metal-free phthalocyanine (available from ORIENT CHEMICAL INDUSTRIES, LTD., OPTRON HPL-X) was used in place of the azo compound of Formula (21) above, as the charge generating material 2.

EXAMPLES 15A TO 19A

Electrophotographic photoreceptors were prepared in the same manner as in Example 14A, except that the X-type metal-free phthalocyanine, in place of the azo compound of Formula (21) above, was used as the charge generating material 2, and exemplary compounds 3, 4, 12, 21, and 23 in Tables 1 and 2, in place of exemplary compound 1 as an asymmetric butadiene-based compound, were used, respectively, as the charge transporting material 3.

EXAMPLE 13B

A single-layered electrophotographic photoreceptor was prepared in the same manner as in Example 13A, except that exemplary compound 1' shown in Table 3 was used in place of exemplary compound 1 as an asymmetric butadiene-based compound as the charge transporting material 3.

EXAMPLE 14B

An electrophotographic photoreceptor was prepared in the same manner as in Example 14A, except that exemplary compound 1' shown in Table 3 was used in place of exemplary compound 1 as an asymmetric butadiene-based compound as the charge transporting material 3.

EXAMPLES 15B TO 19B

Electrophotographic photoreceptors were manufactured in the same manner as in Example 14B, except that exemplary compounds 4', 9', 14', 18', and 26' shown in Tables 3 and 4 were used in place of exemplary compound 1', which is an asymmetrical butadiene-based compound, as a charge transporting material 3, respectively.

COMPARATIVE EXAMPLES 6 AND 7

Electrophotographic photoreceptors were prepared in the same manner as in Example 14A, except that the X-type metal-free phthalocyanine, in place of the azo compound of Formula (21) above, was used as the charge generating material 2, and comparative compound (a) of Formula (18) above and comparative compound (c) of Formula (20) above, in place of exemplary compound 1, were used, respectively, as the charge transporting material 3.

[Evaluation 2]

Initial characteristics and repetition characteristics of the electrophotographic photoreceptors of Examples 7A to 19A and 7B to 19B and Comparative Examples 4 to 7 were evaluated using an electrostatic copying paper testing apparatus (KAWAGUCHI ELECTRIC WORKS CO., LTD., EPA-8200). The evaluation was carried out under the following conditions: 1) normal temperature/normal humidity environments (hereinafter, 'N/N environments') of a temperature of 22° C. and a relative humidity of 65%, and 2) low-temperature/low-humidity environments (hereinafter, 'L/L environments') of a temperature of 10° C. and a relative humidity of 20%.

The initial characteristics evaluation was performed as follows. A surface of each of the electrophotographic receptors was charged by applying a negative voltage of (−) 5 kV, and then a surface potential of the electrophotographic receptor was measured as a charge potential V0 (V). For the single-layered electrophotographic photoreceptor of Examples 13A and 13 B, a positive voltage of (+) 5 kV was applied to charge a surface thereof. Next, the charged surface of each of the electrophotographic photoreceptors was exposed to light. A half-reduction light energy (E½, μJ/cm$^2$), which is defined as a light energy required to reduce the surface potential from the charge potential V0 of the electrophotographic photoreceptor to its half, was used as an evaluation index of sensitivity. A residual potential Vr (V) remaining on the surface of the electrophotographic photoreceptor 10 seconds after the start of the exposure was used as an evaluation index of photoresponsive property. For the electrophotographic photoreceptors of Examples 7A to 12A and 7B to 12B using the azo compound of Formula (21) above as the charge generating material 2 and the electrophotographic photoreceptors of Comparative Examples 4 and 5, white light having an exposure energy of 1 μW/cm$^2$ was used in the exposure process as an exposure light source. For the electrophotographic photoreceptors of Examples 14A to 19A and 14B to 19B and Comparative Example 6 and 7 using X-type metal-free phthalocyanine as the charge generating material 2, light obtained using a monochromater, having an exposure energy of 1 μW/cm$^2$ and a wavelength of 780 nm, was used.

The repetition characteristics evaluation was performed as follows. After 5000 cycles of the above-described charging and exposure process, an half-reduction light energy (E½), a charge potential (V0), and a residual potential (Vr) of each of the electrophotographic photoreceptor were measured in the same manner as in the initial characteristics evaluation.

<Overall Evaluation>

An electrophotographic photoreceptor was evaluated as being very good (VG) when the absolute value |Vr| of Vr as a repetition characteristic was within a range of 10 to 40 both in the N/N environment and in the L/L environment, and as being not bad (NB) when the absolute value |Vr| of Vr as a repetition characteristic in either one of, or in both of, the N/N environment and the L/L environment was outside of the above range, while the absolute value |Vr| in either one of, or in both of, the N/N environment and the L/L environment was 65 or less. These evaluation results are shown in Tables 5A and 5B.

"CGM" and "CTM" in Table 5A each denote a charge generating material and a charge transporting material, respectively. "EX" and "CE" in Table 5A each denote an Example and a Comparative Example, respectively. "AC (21)", "EC", and "CC" each denote an azo compound of Formula (21), an exemplary compound, and a comparative compound, respectively. DMDBDP denotes 3,5-dimethyl-3',5'-di-t-butyldiphenoquinone. In Tables 5A and 5B, the unit of $E_{1/2}$ is MRCM$^2$, and H2Pc denotes an X-type metal-free phthalocyanine.

TABLE 5A

| | | | H/H; 22□/65% | | | | | | L/L; 5° C./20% | | | | |
|---|---|---|---|---|---|---|---|---|---|---|---|---|---|
| | | | Initial Characteristics | | | Repetition Characteristics | | | Initial Characteristics | | | Repetition Characteristics | | |
| CGM | CTM | $E_{1/2}$ | $V_0$ (V) | $V_r$ (V) | $E_{1/2}$ | $V_0$ (V) | $V_r$ (V) | $E_{1/2}$ | $V_0$ (V) | $V_r$ (V) | $E_{1/2}$ | $V_0$ (V) | $V_r$ (V) | |
| EX7A  AC(21) | EC1 | 0.17 | −578 | −19 | 0.21 | −574 | −24 | 0.19 | −580 | −23 | 0.20 | −578 | −25 | VG |
| EX8A  AC(21) | EC3 | 0.18 | −582 | −45 | 0.22 | −576 | −21 | 0.21 | −584 | −21 | 0.23 | −581 | −24 | VG |
| EX9A  AC(21) | EC4 | 0.16 | −580 | −17 | 0.21 | −572 | −22 | 0.20 | −580 | −20 | 0.22 | −576 | −22 | VG |
| EX10A AC(21) | EC12 | 0.19 | −576 | −15 | 0.23 | −570 | −21 | 0.21 | −581 | −19 | 0.23 | −578 | −23 | VG |
| EX11A AC(21) | EC21 | 0.18 | −578 | −13 | 0.22 | −571 | −20 | 0.20 | −583 | −17 | 0.22 | −579 | −20 | VG |
| EX12A AC(21) | EC28 | 0.20 | −582 | −20 | 0.24 | −573 | −28 | 0.23 | −586 | −22 | 0.25 | −583 | −26 | VG |
| CE4   AC(21) | CCa | 0.21 | −583 | −38 | 0.23 | −571 | −37 | 0.43 | −585 | −54 | 0.46 | −582 | −62 | NB |
| CE5   AC(21) | CCc | 0.23 | −589 | −43 | 0.27 | −579 | −56 | 0.46 | −591 | −56 | 0.52 | −588 | −66 | NB |
| EX13A AC(21)/DMDBDP | EC1 | 0.30 | 553 | 30 | 0.35 | 535 | 35 | 0.33 | 550 | 32 | 0.35 | 537 | 35 | VG |
| EX14A H2Pc | EC1 | 0.15 | −582 | −10 | 0.18 | −572 | −15 | 0.17 | −586 | −11 | 0.18 | −583 | −14 | VG |
| EX15A H2Pc | EC3 | 0.16 | −579 | −11 | 0.19 | −570 | −16 | 0.18 | −582 | −14 | 0.19 | −578 | −16 | VG |
| EX16A H2Pc | EC4 | 0.14 | −583 | −13 | 0.16 | −574 | −14 | 0.17 | −585 | −14 | 0.18 | −580 | −18 | VG |
| EX17A H2Pc | EC12 | 0.16 | −579 | −14 | 0.19 | −575 | −29 | 0.19 | −582 | −13 | 0.21 | −578 | −16 | VG |
| EX18A H2Pc** | EC21 | 0.17 | −581 | −12 | 0.20 | −568 | −20 | 0.20 | −586 | −15 | 0.23 | −583 | −17 | VG |
| EX19A H2Pc | EC28 | 0.16 | −579 | −13 | 0.19 | −567 | −21 | 0.21 | −583 | −17 | 0.23 | −578 | −20 | VG |
| CE6   H2Pc | CCa | 0.18 | −576 | −27 | 0.21 | −575 | −30 | 0.38 | −580 | −46 | 0.39 | −575 | −48 | NB |
| CE7   H2Pc | CCc | 0.17 | −583 | −35 | 0.20 | −572 | −42 | 0.39 | −584 | −52 | 0.46 | −579 | −58 | NB |

TABLE 5B

| | | | N/N; 20° C./65% | | | | | | L/L; 5° C./20% | | | | |
|---|---|---|---|---|---|---|---|---|---|---|---|---|---|
| | | | Initial Characteristics | | | Repetition Characteristics | | | Initial Characteristics | | | Repetition Characteristics | | |
| CGM | CTM | $E_{1/2}$ | $V_0$ (V) | $V_r$ (V) | $E_{1/2}$ | $V_0$ (V) | $V_r$ (V) | $E_{1/2}$ | $V_0$ (V) | $V_r$ (V) | $E_{1/2}$ | $V_0$ (V) | $V_r$ (V) | |
| EX7B  AC(21) | EC1' | 0.16 | −577 | −20 | 0.22 | −575 | −25 | 0.20 | −585 | −25 | 0.26 | −581 | −28 | VG |
| EX8B  AC(21) | EC4' | 0.17 | −581 | −27 | 0.21 | −577 | −30 | 0.21 | −588 | −26 | 0.28 | −578 | −30 | VG |
| EX9B  AC(21) | EC9' | 0.18 | −582 | −8 | 0.23 | −576 | −31 | 0.22 | −587 | −24 | 0.27 | −579 | −28 | VG |
| EX10B AC(21) | EC14' | 0.17 | −578 | −20 | 0.21 | −574 | −25 | 0.19 | −586 | −23 | 0.29 | −578 | −29 | VG |
| EX11B AC(21) | EC18' | 0.16 | −579 | −17 | 0.20 | −574 | −24 | 0.19 | −588 | −20 | 0.27 | −580 | −26 | VG |
| EX12B AC(21) | EC26' | 0.19 | −584 | −21 | 0.23 | −578 | −24 | 0.25 | −590 | −24 | 0.29 | −581 | −28 | VG |
| EX13B AC(21)/DMDBDP | EC1' | 0.31 | 551 | 32 | 0.34 | 538 | 37 | 0.35 | 554 | 35 | 0.38 | 548 | 40 | VG |
| EX14B H2Pc | EC1' | 0.14 | −580 | −11 | 0.19 | −575 | −16 | 0.18 | −591 | −14 | 0.21 | −582 | −16 | VG |
| EX15B H2Pc | EC4' | 0.15 | −576 | −14 | 0.20 | −572 | −17 | 0.19 | −588 | −16 | 0.23 | −577 | −18 | VG |
| EX16B H2Pc | EC9' | 0.16 | −582 | −15 | 0.17 | −578 | −18 | 0.19 | −592 | −16 | 0.22 | −579 | −19 | VG |
| EX17B H2Pc | EC14' | 0.17 | −576 | −17 | 0.15 | −570 | −22 | 0.20 | −587 | −18 | 0.24 | −577 | −17 | VG |
| EX18B H2Pc | EC18' | 0.15 | −583 | −15 | 0.21 | −578 | −20 | 0.18 | −592 | −17 | 0.26 | −586 | −19 | VG |
| EX19B H2Pc | EC26' | 0.17 | −584 | −17 | 0.18 | −579 | −24 | 0.22 | −590 | −19 | 0.27 | −576 | −22 | VG |

Referring to Tables 5A and 5B, the electrophotographic photoreceptors of Examples 7A to 12A, 7B to 12B and Examples 14A to 19A and 14B to 19B, including the organic photoconductive material represented by one of Formulae (1) and (1') as the charge transporting material 3, were found to have higher sensitivity due to lower half-reduction light energies (E½), and were found to improve photoresponsive property since the residual potential (Vr) is lower in the negative direction, i.e., the difference between the residual potential (Vr) and the reference potential is smaller, compared to the electrophotographic photoreceptors of Comparative examples 4 to 7 including comparative compound (a) or (c) as the charge transporting material 3, as can be seen from the comparison of the electrophotographic photoreceptors of Examples 7A to 12A and 7B to 12B with Comparative examples 4 and 5 and from the comparison of the electrophotographic photoreceptors of Examples 14A to 19A and 14B to 19B with Comparative examples 6 and 7. These characteristics were also maintained even in case of repeated use, and in particular, even under the L/L environments.

EXAMPLE 20A 9 parts by mass of dendritic titanium oxide (available from ISHIHARA SANGYO KAISHA LTD., TTO-D-1) surface-treated with aluminum oxide ($Al_2O_3$) and zirconium dioxide ($ZrO_2$), and 9 parts by mass of copolymerized nylon resin (available from TORAY INDUSTRIES INC., CM8000) were added to a mixture solvent of 41 parts by mass of 1,3-dioxolane and 41 parts by mass of methanol, and then dispersed using a paint shaker for 8 hours to prepare 0.5 kg of an intermediate layer coating solution. After filling a bath with the intermediate layer coating solution, a hollow-cylindrical electrically conductive aluminum substrate 1 having a diameter of 30 mm, a length of 255 mm, and a thickness of 0.8 mm was dipped in the bath, and then drawing the hollow-cylindrical electrically conductive aluminum substrate 1 up from the bath to form an intermediate layer 8 having a thickness of 1.0 μm on the electrically conductive aluminum substrate 1.

In order to obtain an oxotitanium phthalocyanine as a charge generating material 2, 40 g of o-phthalodinitrile, 18 g of titanium tetrachloride, and 500 mL of α-chloronaphthalene were reacted under a nitrogen atmosphere by heating and stirring at 200° C. to 250° C. for 3 hours, and then left until the temperature cooled down to 100° C. to 130° C., followed by high-temperature filtering, and washing with 200 mL of α-chloronaphthalene that had been heated to 100° C., thereby obtaining a crude product of dichlorotitanyl phthalocyanine. This crude product was washed at room temperature with 200 mL of α-chloronaphthalene and then with 200 ml of methanol, followed by further washing with 500 mL of methanol at a high temperature for 1 hour, and filtering to obtain a crude product. This crude product was washed in 500 mL of ion exchange water by high-temperature washing. The high-temperature washing was repeated until the pH reached 6 to 7 while replacing the used ion exchange water with fresh ion exchange water. The crude product was then dried to obtain oxotitanium phthalocyanine having a crystalline structure which exhibits a sharp diffraction peak at least at a Bragg angle)(2θ±0.2° of 27.2° in a X-ray diffraction spectrum using a Cu-Kα characteristic X-ray having a wavelength of 1.54 Å. Subsequently, 2 parts by mass of the oxo-titanyl phthalocyanine, 1 part by mass of polyvinyl butyral resin (available from SEKISUI CHEMICAL CO., LTD., S-LEC BM-S), and 97 parts by mass of methyl ethyl ketone were mixed together and then dispersed using a paint shaker to prepare 0.5 kg of a charge generating layer coating solution. The charge generating layer coating solution was coated on the intermediate layer 8 by using dip coating method to form a charge generating layer 5 having a thickness of 0.4 μm on the intermediate layer 8.

Next, 10 parts by mass of exemplary compound 1 as an asymmetric butadiene-based compound as the charge transporting material 3, 20 parts by mass of a polycarbonate resin (available from TEIJIN LTD., TS-2040) as a binder resin, 1 part by mass of 2,6-di-t-butyl-4-methyl phenol, and 0.004 parts by mass of dimethyl polysiloxane (available from SHIN-ETSU CHEMICAL CO., LTD., KF-96) were dissolved in 110 parts by mass of THF to prepare 3.0 kg of a charge transporting layer coating solution. The charge transporting layer coating solution was coated on the charge generating layer 5 by using ring coating, and then dried at 130° C. for 1 hour to form a charge transporting layer 6 having a thickness of 20 μm, thereby preparing an electrophotographic photoreceptor.

EXAMPLES 21A AND 22A

Electrophotographic photoreceptors of Examples 21A and 22A were manufactured in the same manner as in Example 20A, except that exemplary compounds 12 and 23 in Tables 1 and 2, which are an asymmetrical butadiene-based compound, were used in place of exemplary compound 1, which is an asymmetrical butadiene-based compound, as a charge transporting material 3, respectively.

EXAMPLES 20B TO 22B

Electrophotographic photoreceptors of Examples 20B to 22B were manufactured in the same manner as in Example 20A, except that exemplary compounds 1', 14', and 26' shown in Tables 3 and 4 were used in place of exemplary compound 1, which is an asymmetrical butadiene-based compound, as a charge transporting material 3, respectively.

COMPARATIVE EXAMPLE 8

An electrophotographic photoreceptor of Comparative Example 8 was manufactured in the same manner as in Example 20A, except that compound (a) represented by Formula (18) was used in place of exemplary compound 1, which is an asymmetrical butadiene-based compound, as a charge transporting material 3.

EXAMPLE 23A

An electrophotographic photoreceptor of Example 23A was manufactured in the same manner as in Example 20A, except that 25 parts by mass of the polycarbonate resin was used as a binder resin in the charge transporting layer 6.

EXAMPLES 24A AND 25A

Electrophotographic photoreceptors of Examples 24A and 25A were manufactured in the same manner as in Example 23A, except that 25 parts by mass of the polycarbonate resin was used as a binder resin in the charge transporting layer 6, and exemplary compounds 12 and 23 in Tables 1 and 2, were respectively used in place of exemplary compound 1, which is an asymmetric butadiene-based compound, as a charge transporting material 3, respectively.

EXAMPLE 23B

An electrophotographic photoreceptor was manufactured in the same manner as in Example 20B, except that 25 parts by mass of the polycarbonate resin was used as a binder resin in the charge transporting layer 6.

EXAMPLES 24B AND 25B

Electrophotographic photoreceptors of Examples 24B and 25B were manufactured in the same manner as in Example 20A, except that exemplary compounds 14', and 26' shown in Tables 3 and 4 were used in place of exemplary compound 1, which is an asymmetrical butadiene-based compound, as a charge transporting material 3, respectively.

REFERENCE EXAMPLE 1A

An electrophotographic photoreceptor was manufactured in the same manner as in Example 20A, except that 10 parts by mass of the polycarbonate resin was used as a binder resin in the charge transporting layer 6.

REFERENCE EXAMPLE 2A

An electrophotographic photoreceptor was manufactured in the same manner as in Example 20A, except that 31 parts by mass of the polycarbonate resin was used as a binder resin in the charge transporting layer 6.

This amount of the polycarbonate resin was not fully dissolved in the same amount of THF as used in Example 20A, when preparing a charge transporting layer solution. For this reason, the amount of THF was increased to obtain a charge transporting layer coating solution in which the polycarbonate resin was fully dissolved. This charge transporting layer coating solution was used to form the charge transporting layer 6.

However, the excessive use of the solvent in the charge transporting layer coating solution caused blushing, i.e., white turbidity on longitudinal end portions of the cylindrical electrophotographic photoreceptor. Accordingly, it was not possible to evaluate the characteristics of the electrophotographic photoreceptor.

REFERENCE EXAMPLE 1B

An electrophotographic photoreceptor was manufactured in the same manner as in Example 20B, except that 10 parts by mass of the polycarbonate resin was used as a binder resin in the charge transporting layer 6.

REFERENCE EXAMPLE 2B

An electrophotographic photoreceptor was manufactured in the same manner as in Example 20B, except that 31 parts by mass of the polycarbonate resin was used as a binder resin in the charge transporting layer 6.

This amount of the polycarbonate resin was not fully dissolved in the same amount of THF as used in Example 20B, when preparing a charge transporting layer solution. For this reason, the amount of THF was increased to obtain a charge transporting layer coating solution in which the polycarbonate resin was fully dissolved. This charge transporting layer coating solution was used to form the charge transporting layer 6.

However, the excessive use of the solvent in the charge transporting layer coating solution caused blushing, i.e., white turbidity on longitudinal end portions of the cylindrical electrophotographic photoreceptor. Accordingly, it was not possible to evaluate the characteristics of the electrophotographic photoreceptor.

[Evaluation 3]

The wear-resistance and the stability of electrical characteristics of the electrophotographic photoreceptors of Examples 20A to 25A and 20B to 25B, Comparative Example 8, and Reference Examples 1A, 1B, 2A and 2B were evaluated as follows.

Each of the electrophotographic photoreceptors was mounted on a digital copier (available from SAMSUNG ELECTRONICS Co., Ltd., MultiXpress C8650DN). A thickness dl of the photosensitive layer after forming images on 40,000 sheets was measured, and a thickness difference $\Delta d$ (=d0-d1) between the thickness dl and an initial thickness d0 of the photosensitive layer before use was used as an evaluation index of wear-resistance.

A surface potentiometer (available from GENTEC INC., CATE751) was mounted in the digital copier to measure surface potentials of each of the electrophotographic photoreceptors during an imaging process in the N/N environments (22° C./65% RH), i.e., a charge potential V0(V) as a surface potential immediately after charging, and a surface potential VL(V) immediately after exposure to laser light.

A surface potential VL (V) immediately after exposure to laser light in the L/L environments (10° C./20% RH) was performed in the same manner as above. Next, a potential variation $\Delta VL(=VL(2)-VL(1))$, where VL(1) denotes the surface potential VL in the N/N environments, and VL(2) denotes the surface potential VL in the L/L environments, i.e., a difference between VL(1) and VL(2), was obtained as an evaluation index of electrical characteristics stability. The surface charging of the electrophotographic photoreceptors was performed by negative charging. The evaluation results are shown in Tables 6A and 6B.

An electrophotographic photoreceptor having a thickness reduction $\Delta d$ of 5 or less and an absolute value $|\Delta VL|$ of a L/L-N/N potential variation of 20 or greater was considered to be very good (VG). Otherwise, an electrophotographic photoreceptor was considered to be not bad (NB).

TABLE 6A

| | Charge Transporting Material | Charge Transporting Material/Binder Resin | Film Reduction $\Delta d(\mu m)$ | N/N-Potential Characteristics | | L/L-Potential Characteristics | Overall Evaluation |
|---|---|---|---|---|---|---|---|
| | | | | $V_0$ (V) | $V_L$ (V) | $\Delta V_L$ (V) | |
| EX 20A | EC 1 | 10/20 | 3.2 | −550 | −38 | −27 | VG |
| EX 21A | EC 12 | 10/20 | 3.1 | −542 | −35 | −23 | VG |
| EX 22A | EC 23 | 10/20 | 3.3 | −545 | −33 | −28 | VG |
| CE 8 | CC a | 10/20 | 4.3 | −534 | −100 | −73 | VG |
| EX 23A | EC 1 | 10/25 | 2.5 | −540 | −45 | −36 | VG |

TABLE 6A-continued

| Charge Transporting Material | Charge Transporting Material/Binder Resin | Film Reduction $\Delta d(\mu m)$ | N/N-Potential Characteristics | | L/L-Potential Characteristics | Overall Evaluation |
|---|---|---|---|---|---|---|
| | | | $V_0$ (V) | $V_L$ (V) | $\Delta V_L$ (V) | |
| EX 24A EC 12 | 10/25 | 2.4 | −545 | −42 | −35 | VG |
| EX 25A EC 23 | 10/25 | 2.6 | −543 | −41 | −37 | VG |
| RE 1A EC 1 | 10/10 | 12.2 | −523 | −19 | −13 | NB |
| RE 2A EC 1 | 10/31 | — | — | — | — | — |

(EX: Example,
CE: Comparative Example,
RE: Reference Example,
EC: Exemplary Compound,
CC: Comparative Compound)

TABLE 6B

| Charge Transporting Material | Charge Transporting Material/Binder Resin | Film Reduction $\Delta d(\mu m)$ | N/N-Potential Characteristics | | L/L-Potential Characteristics | Overall Evaluation |
|---|---|---|---|---|---|---|
| | | | $V_0$ (V) | $V_L$ (V) | $\Delta V_L$ (V) | |
| EX 20B EC 1' | 10/20 | 3.8 | −554 | −38 | −28 | VG |
| EX 21B EC 14' | 10/20 | 4.0 | −546 | −36 | −25 | VG |
| EX 22B EC 26' | 10/20 | 4.1 | −543 | −36 | −27 | VG |
| EX 23B EC 1' | 10/25 | 2.7 | −542 | −46 | −34 | VG |
| EX 24B EC 14' | 10/25 | 2.8 | −546 | −43 | −36 | VG |
| EX 25B EC 26' | 10/25 | 2.9 | −543 | −42 | −34 | VG |
| RE 1B EC 1' | 10/10 | 12.2 | −532 | −20 | −15 | NB |
| RE 2B EC 1' | 10/31 | — | — | — | — | — |

Referring to Tables 6A and 6B, the electrophotographic photoreceptors of Examples 20A to 25A and 20B to 25B and Reference Examples 1A and 1B, which include the organic photoconductive material of one of Formulae (1) and (1') as a charge transporting material 3, even when a higher proportion of the binder resin is used, have a smaller magnitude of the surface potentials VL in the N/N environments and accordingly an improved photoresponsive properties, compared to the electrophotographic photoreceptor of Comparative Example 8 including comparative compound (a) as a charge transporting material. Also, the electrophotographic photoreceptors of Examples 20A to 25A and 20B to 25B and Reference Examples 1A and 1B have a smaller magnitude of the potential variation ΔVL, and accordingly, have sufficient photoresponsive properties even in the L/L environments.

In the electrophotographic photoreceptors of Examples 20A to 25A and 20B to 25B in which a mass ratio (A:B) of the charge transporting material (A) to the binder resin (B) was in a range of 10:12 to 10:30, it was found that their thickness reductions Δd in the photosensitive layers were smaller than that in the electrophotographic photoreceptor of Reference Examples 1A and 1B using a relatively low proportion of the binder resin, i.e., using a mass ratio (A:B) of the charge transporting material (A) to the binder resin (B) of 10:10, which is beyond the mass ratio (A:B) of 10:12. Accordingly, the electrophotographic photoreceptors of Examples 20A to 25A and 20B to 25B had an improved wear-resistance, as compared with the electrophotographic photoreceptor of Reference Example 1A and 1B.

As described above, the wear-resistance of the charge transporting layer was improved without deterioration in the photoresponsive property by using the organic photoconductive material of one of Formulae (1) and (1').

INDUSTRIAL APPLICABILITY

The present disclosure may be applied to an organic photoconductive material, an electrophotographic photoreceptor including the organic photoconductive material, and an electrophotographic imaging apparatus including the electrophotographic photoreceptor.

SEQUENCE LIST FREE TEXT

None

The invention claimed is:

1. An asymmetric butadiene-based charge transporting compound represented by one of Formulae (1) and (1'):

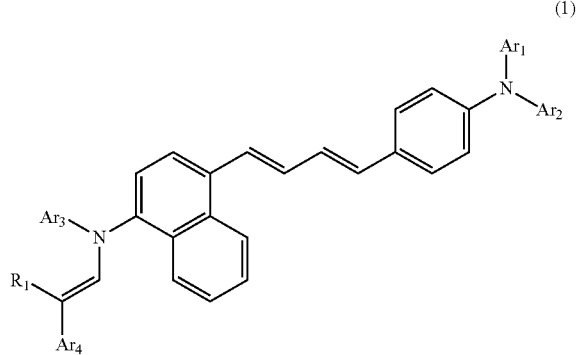

(1)

-continued (1')

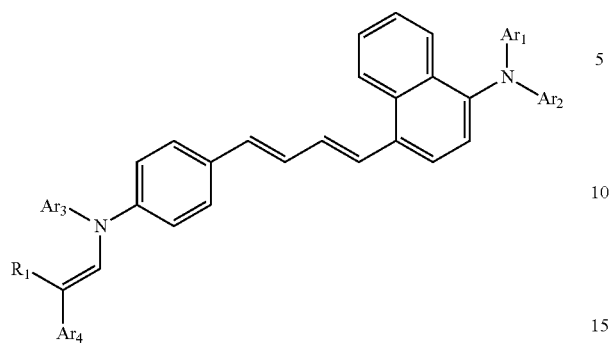

wherein Ar$_1$, Ar$_2$, Ar$_3$, and Ar$_4$ are each independently a substituted or unsubstituted aryl group or a substituted or unsubstituted heteroaryl group, and R1 is independently a substituted or unsubstituted aryl group, a substituted or unsubstituted heteroaryl group, a substituted or unsubstituted aralkyl group, or a substituted or unsubstituted alkyl group.

2. The asymmetric butadiene-based charge transporting compound of claim 1, wherein the asymmetric butadiene-based charge transporting compounds of Formulae (1) and (1') are represented by Formulae (2) and (2'), respectively:

(2)

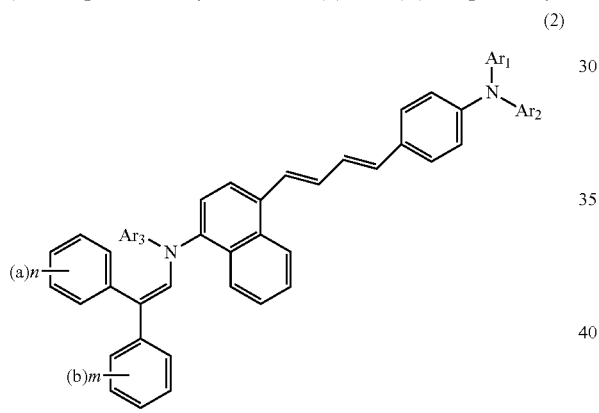

-continued (2')

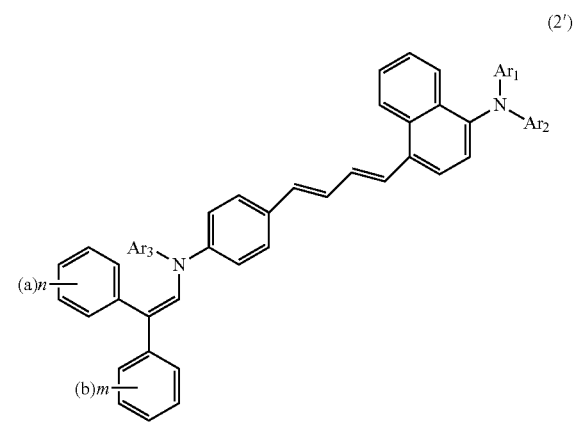

wherein a and b are each independently a hydrogen atom, an alkyl group, an alkoxy group, or a dialkylamino group, m and n are each independently an integer selected from 1 to 5, and Ar$_1$, Ar$_2$, Ar$_3$, and Ar$_4$ are the same as defined in claim 1.

3. The asymmetric butadiene-based charge transporting compound of claim 1, wherein the asymmetric butadiene-based charge transporting compounds of Formulae (1) and (1') are represented by Formulae (3) and (3'), respectively:

(3)

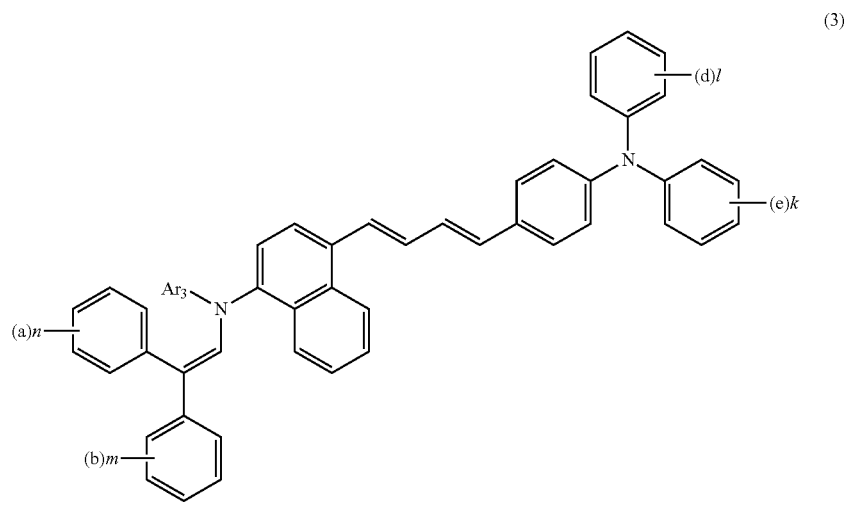

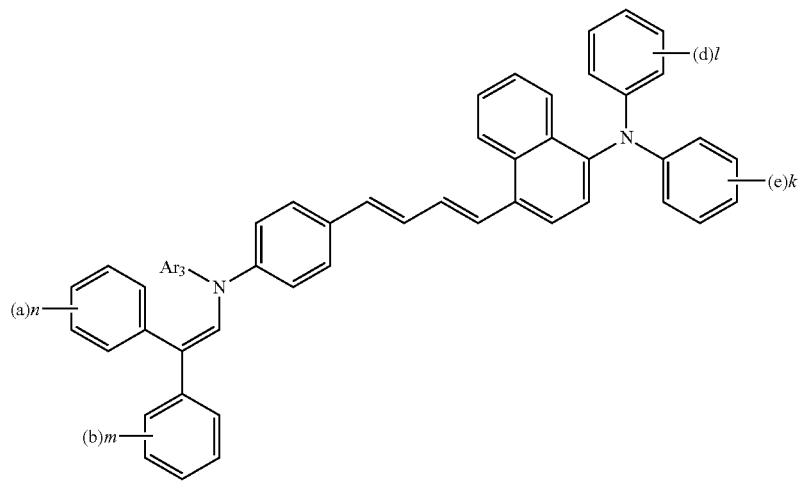
(3')

wherein a, b, d, and e are each independently a hydrogen atom, an alkyl group, an alkoxy group, or a dialkylamino group, l, k, m, and n are each independently an integer selected from 1 to 5, and Ar$_3$ is the same as defined in claim 1.

4. An electrophotographic photoreceptor comprising a laminated photosensitive layer or a single-layered photosensitive layer on an electrically conductive substrate, the laminated photosensitive layer comprising a charge generating layer comprising a charge generating material and a charge transporting layer comprising a charge transporting material that are sequentially laminated in the stated order, the single-layered photosensitive layer comprising a charge generating material and a charge transporting material, wherein the charge transporting layer or the single-layered photosensitive layer comprises at least one asymmetric butadiene-based compound as the charge transporting material, wherein the asymmetric butadiene-based compound is represented by one of Formulae (1) and (1'):

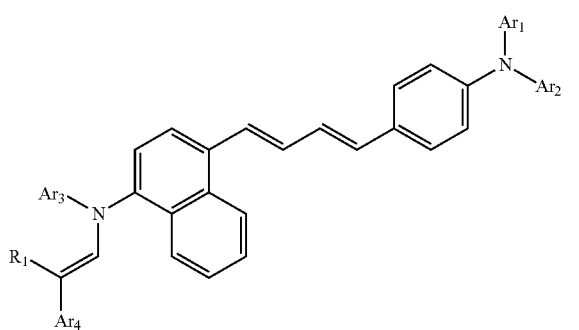
(1)

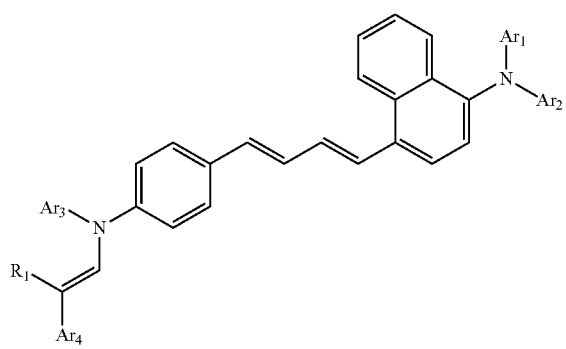
(1')

wherein Ar$_1$, Ar$_2$, Ar$_3$, and Ar$_4$ are each independently a substituted or unsubstituted aryl group or a substituted or unsubstituted heteroaryl group, and R1 is independently a substituted or unsubstituted aryl group, a substituted or unsubstituted heteroaryl group, a substituted or unsubstituted aralkyl group, or a substituted or unsubstituted alkyl group.

5. The electrophotographic photoreceptor of claim 4, wherein the asymmetric butadiene-based compounds of Formulae (1) and (1') are represented by Formulae (2) and (2'), respectively:

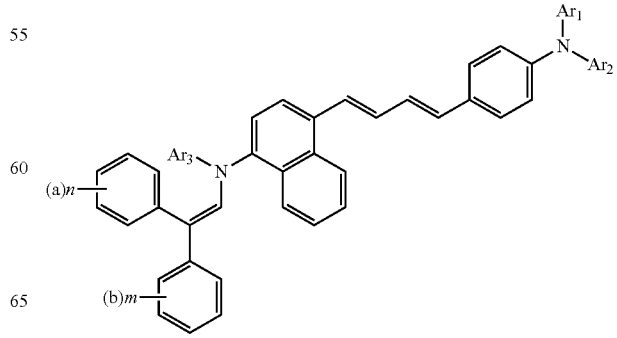
(2)

-continued

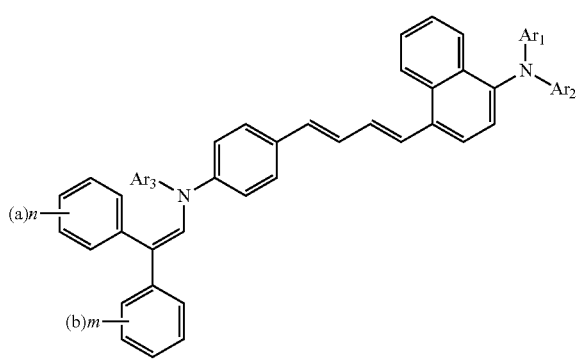
(2')

wherein a and b are each independently a hydrogen atom, an alkyl group, an alkoxy group, or a dialkylamino group, m and n are each independently an integer selected from 1 to 5, and $Ar_1$, $Ar_2$, $Ar_3$, and $Ar_4$ are the same as defined in claim 1.

6. The electrophotographic photoreceptor of claim 4, wherein the asymmetric butadiene-based compounds of Formulae (1) and (1') are represented by Formulae (3) and (3'), respectively:

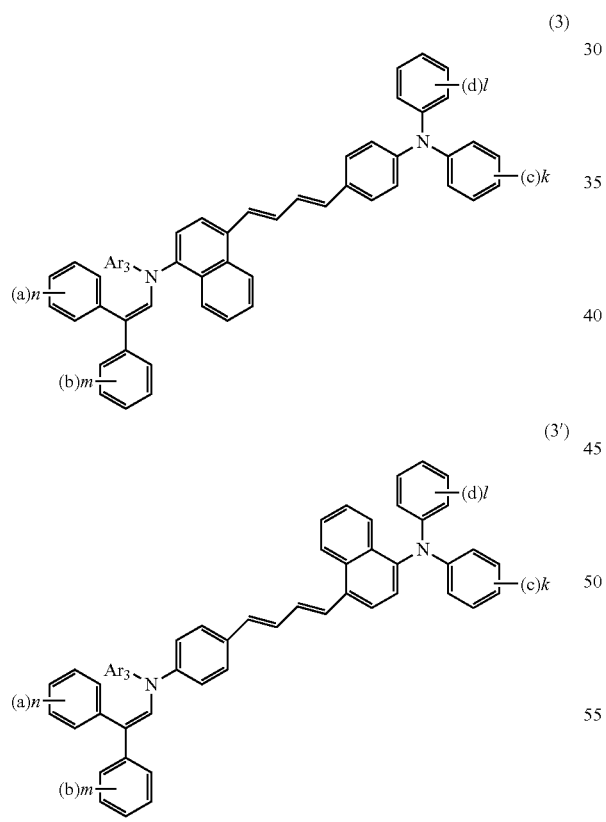

wherein a, b, d, and e are each independently a hydrogen atom, an alkyl group, an alkoxy group, or a dialkylamino group, l, k, m, and n are each independently an integer selected from 1 to 5, and $Ar_3$ is the same as defined in claim 1.

7. The electrophotographic photoreceptor of claim 4, wherein the charge transporting layer or the single-layered photosensitive layer further comprises a binder resin, wherein a mass ratio (A:B) of the charge transporting material (A) to the binder resin (B) contained in the charge transporting layer or the single-layered photosensitive layer is in a range of about 10:12 to about 10:30.

8. The electrophotographic photoreceptor of claim 4, wherein the charge generating layer or the single-layered photosensitive layer comprises oxotitanium phthalocyanine, which exhibits a diffraction peak at least at a Bragg angle) (2θ±0.2° of about 27.2° in a characteristic X-ray diffraction of Cu-Kα having a wavelength of about 1.54 Å, as the charge generating material.

9. The electrophotographic photoreceptor of claim 4, further comprising an intermediate layer between either the laminated photosensitive layer or the single-layered photosensitive layer and the electrically conductive substrate.

10. An electrophotographic imaging apparatus comprising an electrophotographic photoreceptor, wherein the electrophotographic photoreceptor comprises a laminated photosensitive layer or a single-layered photosensitive layer on an electrically conductive substrate, the laminated photosensitive layer comprising a charge generating layer comprising a charge generating material and a charge transporting layer comprising a charge transporting material that are sequentially laminated in the stated order, the single-layered photosensitive layer comprising a charge generating material and a charge transporting material, wherein the charge transporting layer or the single-layered photosensitive layer comprises at least one asymmetric butadiene-based compound as the charge transporting material, wherein the asymmetric butadiene-based compound is represented by one of Formulae (1) and (1'):

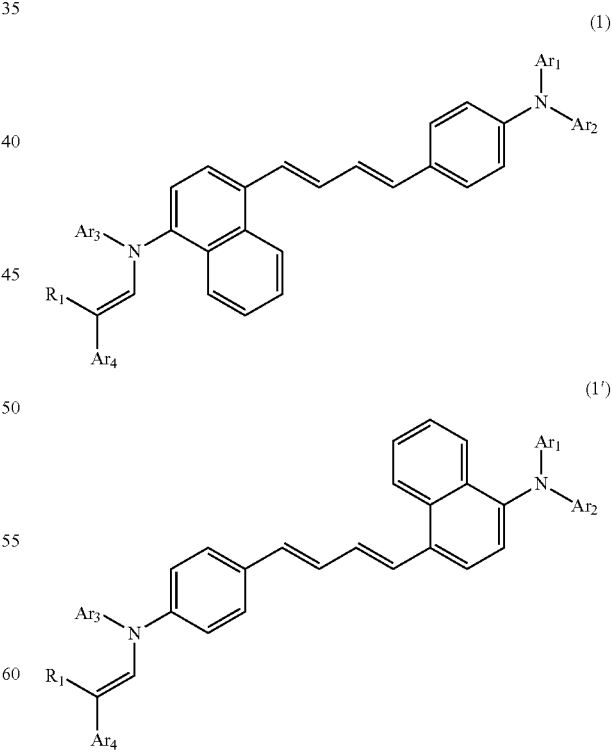

wherein $Ar_1$, $Ar_2$, $Ar_3$, and $Ar_4$ are each independently a substituted or unsubstituted aryl group or a substituted or unsubstituted heteroaryl group, and R1 is independently a substituted or unsubstituted aryl group, a substituted or unsubstituted heteroaryl group, a substituted or unsubstituted aralkyl group, or a substituted or unsubstituted alkyl group.

11. The electrophotographic imaging apparatus of claim 10, wherein the asymmetric butadiene-based compounds of Formulae (1) and (1') are represented by Formulae (2) and (2'), respectively:

(2)

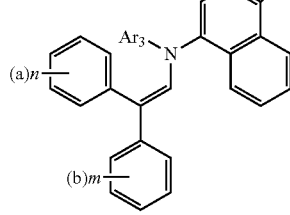

(2')

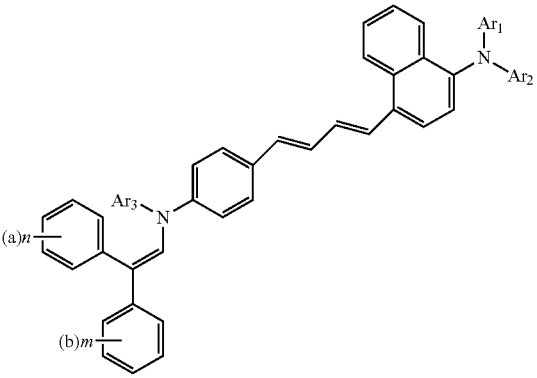

wherein a and b are each independently a hydrogen atom, an alkyl group, an alkoxy group, or a dialkylamino group, m and n are each independently an integer selected from 1 to 5, and $Ar_1$, $Ar_2$, $Ar_3$, and $Ar_4$ are the same as defined in claim 1.

12. The electrophotographic imaging apparatus of claim 10, wherein the asymmetric butadiene-based compounds of Formulae (1) and (1') are represented by Formulae (3) and (3'), respectively:

(3)

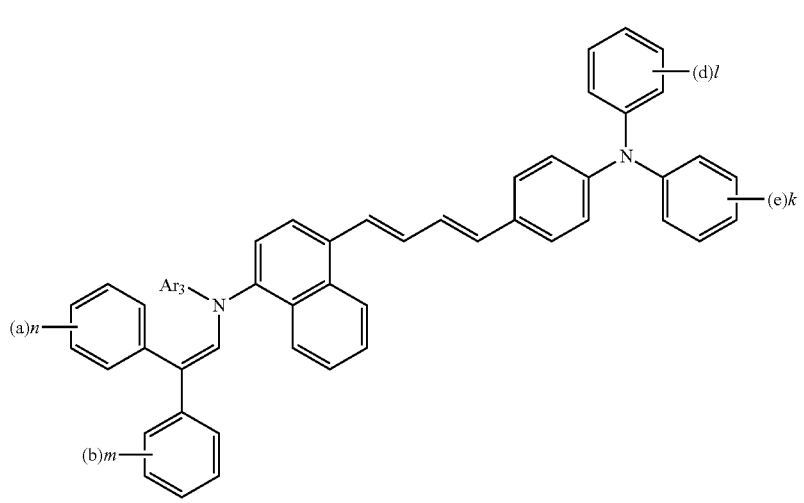

(3')

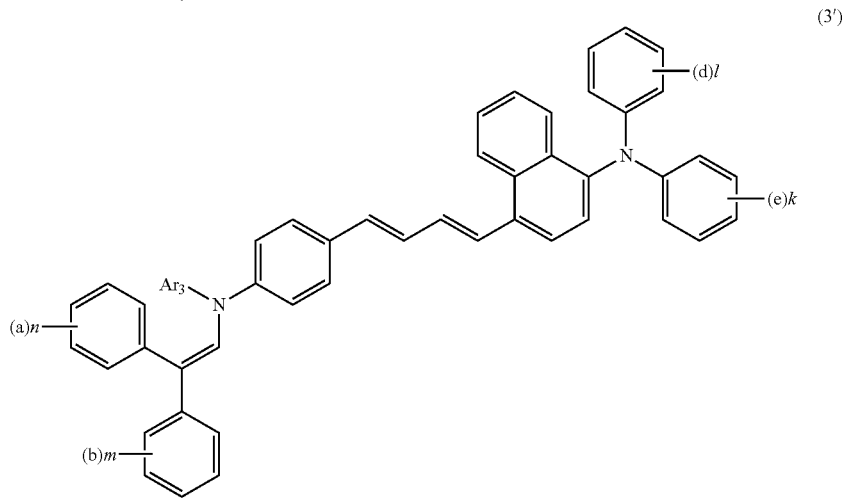

wherein a, b, d, and e are each independently a hydrogen atom, an alkyl group, an alkoxy group, or a dialkylamino group, l, k, m, and n are each independently an integer selected from 1 to 5, and $Ar_3$ is the same as defined in claim 1.

13. The electrophotographic imaging apparatus of claim 10, wherein the charge transporting layer or the single-layered photosensitive layer further comprises a binder resin, wherein a mass ratio (A:B) of the charge transporting material (A) to the binder resin (B) contained in the charge transporting layer or the single-layered photosensitive layer is in a range of about 10:12 to about 10:30.

14. The electrophotographic imaging apparatus of claim 10, wherein the charge generating layer or the single-layered photosensitive layer comprises oxotitanium phthalocyanine, which exhibits a diffraction peak at least at a Bragg angle) (2θ±0.2° of about 27.2° in a characteristic X-ray diffraction of Cu-Kα having a wavelength of about 1.54 Å, as the charge generating material.

15. The electrophotographic imaging apparatus of claim 10, wherein the electrophotographic photoreceptor further comprises an intermediate layer between either the laminated photosensitive layer or the single-layered photosensitive layer and the electrically conductive substrate.

16. The electrophotographic imaging apparatus of claim 10, forming an image through a phase inversion development process.

\* \* \* \* \*